(12) United States Patent
Jensen et al.

(10) Patent No.: US 7,446,179 B2
(45) Date of Patent: *Nov. 4, 2008

(54) CD19-SPECIFIC CHIMERIC T CELL RECEPTOR

(75) Inventors: Micahel C. Jensen, Pasadena, CA (US); Stephen Forman, San Marino, CA (US); Andrew Raubitschek, San Marino, CA (US)

(73) Assignee: City of Hope, Duarte, CA (US)

( * ) Notice: Subject to any disclaimer, the term of this patent is extended or adjusted under 35 U.S.C. 154(b) by 514 days.

This patent is subject to a terminal disclaimer.

(21) Appl. No.: 10/416,011

(22) PCT Filed: Nov. 7, 2001

(86) PCT No.: PCT/US01/42997

§ 371 (c)(1),
(2), (4) Date: May 7, 2003

(87) PCT Pub. No.: WO02/077029

PCT Pub. Date: Oct. 3, 2002

(65) Prior Publication Data

US 2004/0126363 A1 Jul. 1, 2004

Related U.S. Application Data

(60) Provisional application No. 60/246,117, filed on Nov. 7, 2000.

(51) Int. Cl.
C12P 21/08 (2006.01)

(52) U.S. Cl. .................. 530/387.3; 435/328; 435/344.1

(58) Field of Classification Search ....................... None
See application file for complete search history.

(56) References Cited

U.S. PATENT DOCUMENTS

| 5,359,046 A | 10/1994 | Capon et al. |
| 5,712,149 A | 1/1998 | Roberts |
| 6,410,319 B1 * | 6/2002 | Raubitschek et al. ..... 435/343.1 |

FOREIGN PATENT DOCUMENTS

| WO | WO 94/11026 A2 | 5/1994 |
| WO | WO 97/23613 A2 | 7/1997 |
| WO | WO 98/41613 A1 | 9/1998 |
| WO | WO 99/54440 A1 | 10/1999 |
| WO | WO 00/23573 A2 | 4/2000 |
| WO | WO 00/23573 A3 | 4/2000 |
| WO | WO 00/31239 A1 | 6/2000 |

OTHER PUBLICATIONS

Jensen et. al. CD20 is a molecular target for . . . implications for cellular immunotherapy of CD20+ malignancy. Biology of Blood and Marrow Transplantation. 1998; 4: 75-8.*

Stamenkovic et. al. CD19, the earliest differentiation antigen of the B cell lineage . . . epstein-barr virus-related cytoplasmic tail. J. Exp. Med. 1988; 168: 1205-1210.*

Whitlow et al., Protein Eng. Nov. 1993;6(8):989-95.*

Jensen, M et al. "CD20 Is A Molecular Target For scFvFc:ζ Receptor Redirected T Cells: Implications For Cellular Immunotherapy of CD2+ Malignancy," *Biology of Blood and Marrow Transplantation*, 4:75-83, 1998.

Abken, H. et al. "Chimeric T-Cell Receptors: Highly Specific Tools To Target Cytotoxic T-Lymphocytes To Tumour Cells," *Cancer Treatment Reviews*, 23:97-112, 1997.

Nicholson, Ian C. et al. "Construction And Characterisation Of A Functional CD19 Specific Single Chain Fv Fragment . . .," *Molecular Immunology*, vol. 34, No. 16-17, 1157-1165, 1997.

Amstutz, H., et al. "Production And Characterization Of A Mouse/Human Chimeric Antibody Directed Against Human Neuroblastoma,", Int. J. Cancer, 53: 147-152, 1993.

Kipriyanov, S. M. et al. "Bispecific CD3 × CD19 Diabody For T Cell-Mediated Lysis of Malignant Human B Cells", *International Journal of Cancer*, vol. 77, No. 5, 763-771, 1998.

Abken, H. et al. "Can Combined T-cell And Antibody-Based Immunotherapy Outsmart Tumor Cells?," *Immunology Today*, vol. 19, No. 1, 1-5, 1998.

Haisma, H. et al. "Construction And Characterization Of A Fusion Protein Of Single-Chain Anti-CD20 Antibody And Human Beta-Glucuronidase For Antibody-Directed Enzyme Prodrug Therapy," *Blood*, vol. 92, No. 1, 184-190, 1998.

Anderson, D. et al. "Targeted Anti-Cancer Therapy Using Rituximab, A Chimaeric Anti-CD20 Antibody (IDEC-C2B8) In The Treatment of Non-Hodgkin's B-Cell Lymphoma", *Biochemical Society Transactions*, vol. 25, 705-8, 1997.

* cited by examiner

*Primary Examiner*—Eileen B. O'Hara
*Assistant Examiner*—Zachary Skelding
(74) *Attorney, Agent, or Firm*—Rothwell, Figg, Ernst & Manbeck p.c.

(57) ABSTRACT

The present invention relates to a genetically engineered, CD19-specific chimeric T cell receptor and to immune cells expressing the chimeric receptor The present invention also relates to the use of such cells for cellular immunotherapy of CD9+ malignancies and for abrogating any untoward B cell function. The chimeric receptor is a single chain scFvFc:ζ receptor where scFvFc designates the extracellular domain, scFv designates the $V_H$ and $V_L$ chains of a single chain monoclonal antibody to CD19, Fc represents at least part of a constant region of an IgG$_1$, and ζ represents the intracellular signaling domain of the zeta chain of human CD3. The extracellular domain scFvFc and the intracellular domain ζ are linked by a transmembrane domain such as the transmembrane domain of CD4. In one aspect, the chimeric receptor comprises amino acids 23-634 of SEQ I DNO:2. The present invention further relates to a method of making a redirected T cell expressing a chimeric T cell receptor by electroporation using naked DNA encoding the receptor.

5 Claims, 10 Drawing Sheets

```
         XbaI            (hGMCSF signal peptide-)
       ~~~~~~          M  L  L  V  T  S   L  L  L  C   E  L  P
   1 ATCTCTAGAG CCGCCACCAT GCTTCTCCTG GTGACAAGCC TTCTGCTCTG TGAGTTACCA
     TAGAGATCTC GGCGGTGGTA CGAAGAGGAC CACTGTTCGG AAGACGAGAC ACTCAATGGT (V_L-)
      H  P  A   F  L  L  I   P  D  I   Q  M  T   Q  T  T  S   S  L  S
  61 CACCCAGCAT TCCTCCTGAT CCCAGACATC CAGATGACAC AGACTACATC CTCCCTGTCT
     GTGGGTCGTA AGGAGGACTA GGGTCTGTAG GTCTACTGTG TCTGATGTAG GAGGGACAGA A  S  L   G  D  R  V   T  I  S   C  R  A   S  Q  D  I   S  K  Y
 121 GCCTCTCTGG GAGACAGAGT CACCATCAGT TGCAGGGCAA GTCAGGACAT TAGTAAATAT
     CGGAGAGACC CTCTGTCTCA GTGGTAGTCA ACGTCCCGTT CAGTCCTGTA ATCATTTATA L  N  W   Y  Q  Q  K   P  D  G   T  V  K   L  L  I  Y   H  T  S
 181 TTAAATTGGT ATCAGCAGAA ACCAGATGGA ACTGTTAAAC TCCTGATCTA CCATACATCA
     AATTTAACCA TAGTCGTCTT TGGTCTACCT TGACAATTTG AGGACTAGAT GGTATGTAGT R  L  H   S  G  V  P   S  R  F   S  G  S   G  S  G  T   D  Y  S
 241 AGATTACACT CAGGAGTCCC ATCAAGGTTC AGTGGCAGTG GGTCTGGAAC AGATTATTCT
     TCTAATGTGA GTCCTCAGGG TAGTTCCAAG TCACCGTCAC CCAGACCTTG TCTAATAAGA L  T  I   S  N  L  E   Q  E  D   I  A  T   Y  F  C  Q   Q  G  N
 301 CTCACCATTA GCAACCTGGA GCAAGAAGAT ATTGCCACTT ACTTTTGCCA ACAGGGTAAT
     GAGTGGTAAT CGTTGGACCT CGTTCTTCTA TAACGGTGAA TGAAAACGGT TGTCCCATTA (Whitlow linker-)
      T  L  P   Y  T  F  G   G  G  T   K  L  E   I  T  G  S   T  S  G
 361 ACGCTTCCGT ACACGTTCGG AGGGGGGACT AAGTTGGAAA TAACAGGCTC CACCTCTGGA
     TGCGAAGGCA TGTGCAAGCC TCCCCCCTGA TTCAACCTTT ATTGTCCGAG GTGGAGACCT (V_H-)
      S  G  K   P  G  S  E  G  S   T  K  G   E  V  K  L   Q  E  S
 421 TCCGGCAAGC CCGGATCTGG CGAGGGATCC ACCAAGGGCG AGGTGAAACT GCAGGAGTCA
     AGGCCGTTCG GGCCTAGACC GCTCCCTAGG TGGTTCCCGC TCCACTTTGA CGTCCTCAGT G  P  G   L  V  A  P   S  Q  S   L  S  V   T  C  T  V   S  G  V
 481 GGACCTGGCC TGGTGGCGCC CTCACAGAGC CTGTCCGTCA CATGCACTGT CTCAGGGGTC
     CCTGGACCGG ACCACCGCGG GAGTGTCTCG GACAGGCAGT GTACGTGACA GAGTCCCCAG S  L  P   D  Y  G  V   S  W  I   R  Q  P   P  R  K  G   L  E  W
 541 TCATTACCCG ACTATGGTGT AAGCTGGATT CGCCAGCCTC CACGAAAGGG TCTGGAGTGG
     AGTAATGGGC TGATACCACA TTCGACCTAA GCGGTCGGAG GTGCTTTCCC AGACCTCACC L  G  V   I  W  G  S   E  T  T   Y  Y  N   S  A  L  K   S  R  L
 601 CTGGGAGTAA TATGGGGTAG TGAAACCACA TACTATAATT CAGCTCTCAA ATCCAGACTG
     GACCCTCATT ATACCCCATC ACTTTGGTGT ATGATATTAA GTCGAGAGTT TAGGTCTGAC T  I  I   K  D  N  S   K  S  Q   V  F  L   K  M  N  S   L  Q  T
 661 ACCATCATCA AGGACAACTC CAAGAGCCAA GTTTTCTTAA AAATGAACAG TCTGCAAACT
     TGGTAGTAGT TCCTGTTGAG GTTCTCGGTT CAAAAGAATT TTTACTTGTC AGACGTTTGA D  D  T   A  I  Y  Y   C  A  K   H  Y  Y   Y  G  G  S   Y  A  M
 721 GATGACACAG CCATTTACTA CTGTGCCAAA CATTATTACT ACGGTGGTAG CTATGCTATG
     CTACTGTGTC GGTAAATGAT GACACGGTTT GTAATAATGA TGCCACCATC GATACGATAC
```

FIG. 1A

```
                                                         (hingeF_I-)
        D  Y  W    G  Q  G  T    S  V  T    V  S  S    V  E  P  K    S  S  D
   781  GACTACTGGG GTCAAGGAAC CTCAGTCACC GTCTCCTCAG TAGAACCCAA ATCTTCTGAC
        CTGATGACCC CAGTTCCTTG GAGTCAGTGG CAGAGGAGTC ATCTTGGGTT TAGAAGACTG K  T  H  T    C  P  P    C  P  A    P  E  L    L  G  G  P    S  V  F
   841  AAAACTCACA CGTGCCCACC GTGCCCAGCA CCTGAACTCC TGGGGGGACC GTCAGTCTTC
        TTTTGAGTGT GCACGGGTGG CACGGGTCGT GGACTTGAGG ACCCCCCTGG CAGTCAGAAG L  T  P    P  K  P  K    D  T  L    M  I  S    R  T  P  E    V  T  C
   901  CTCTTCCCCC CAAAACCCAA GGACACCCTC ATGATCTCCC GGACCCCTGA GGTCACATGC
        GAGAAGGGGG GTTTTGGGTT CCTGTGGGAG TACTAGAGGG CCTGGGGACT CCAGTGTACG V  V  V    D  V  S  H    E  D  P    E  V  K    F  N  W  Y    V  D  G
   961  GTGGTGGTGG ACGTGAGCCA CGAAGACCCT GAGGTCAAGT TCAACTGGTA CGTGGACGGC
        CACCACCACC TGCACTCGGT GCTTCTGGGA CTCCAGTTCA AGTTGACCAT GCACCTGCCG V  E  V    H  N  A  K    T  K  P    R  E  E    Q  Y  N  S    T  Y  R
  1021  GTGGAGGTGC ATAATGCCAA GACAAAGCCG CGGGAGGAGC AGTACAACAG CACGTACCGT
        CACCTCCACG TATTACGGTT CTGTTTCGGC GCCCTCCTCG TCATGTTGTC GTGCATGGCA V  V  S    V  L  T  V    L  H  Q    D  W  L    N  G  K  E    Y  K  C
  1081  GTGGTCAGCG TCCTCACCGT CCTGCACCAG GACTGGCTGA ATGGCAAGGA GTACAAGTGC
        CACCAGTCGC AGGAGTGGCA GGACGTGGTC CTGACCGACT TACCGTTCCT CATGTTCACG K  V  S    N  K  A  L    P  A  P    I  E  K    T  I  S  K    A  K  G
  1141  AAGGTCTCCA ACAAAGCCCT CCCAGCCCCC ATCGAGAAAA CCATCTCCAA AGCCAAAGGG
        TTCCAGAGGT TGTTTCGGGA GGGTCGGGGG TAGCTCTTTT GGTAGAGGTT TCGGTTTCCC Q  P  R    E  P  Q  V    Y  T  L    P  P  S    R  D  E  L    T  K  N
  1201  CAGCCCCGAG AACCACAGGT GTACACCCTG CCACCATCAC GAGATGAGCT GACCAAGAAC
        GTCGGGGCTC TTGGTGTCCA CATGTGGGAC GGTGGTAGTG CTCTACTCGA CTGGTTCTTG Q  V  S    L  T  C  L    V  K  G    F  Y  P    S  D  I  A    V  E  W
  1261  CAGGTCAGCC TGACCTGCCT GGTCAAAGGC TTCTATCCCA GCGACATCGC CGTGGAGTGG
        GTCCAGTCGG ACTGGACGGA CCAGTTTCCG AAGATAGGGT CGCTGTAGCG GCACCTCACC E  S  N    G  Q  P  E    N  N  Y    K  T  T    P  P  V  L    D  S  D
  1321  GAGAGCAATG GGCAGCCGGA GAACAACTAC AAGACCACGC CTCCCGTGCT GGACTCCGAC
        CTCTCGTTAC CCGTCGGCCT CTTGTTGATG TTCTGGTGCG GAGGGCACGA CCTGAGGCTG G  S  F    F  L  Y  S    K  L  T    V  D  K    S  R  W  Q    Q  G  N
  1381  GGCTCCTTCT TCCTCTACAG CAAGCTCACC GTGGACAAGA GCAGGTGGCA GCAGGGGAAC
        CCGAGGAAGA AGGAGATGTC GTTCGAGTGG CACCTGTTCT CGTCCACCGT CGTCCCCTTG V  F  S    C  S  V  M    H  E  A    L  H  N    H  Y  T  Q    K  S  L
  1441  GTCTTCTCAT GCTCCGTGAT GCATGAGGCT CTGCACAACC ACTACACGCA GAAGAGCCTC
        CAGAAGAGTA CGAGGCACTA CGTACTCCGA GACGTGTTGG TGATGTGCGT CTTCTCGGAG S  L  S    P  G  K  M    A  L  I    V  L  G    G  V  A  G    L  L  L
  1501  TCCCTGTCTC CCGGGAAAAT GGCCCTGATT GTGCTGGGGG GCGTCGCCGG CCTCCTGCTT
        AGGGACAGAG GGCCCTTTTA CCGGGACTAA CACGACCCCC CGCAGCGGCC GGAGGACGAA
```

FIG. 1B

```
              F  I  G    L  G  I  F    F  R  V    K  F  S    R  S  A  D    A  P  A
    1561 TTCATTGGGC TAGGCATCTT CTTCAGAGTG AAGTTCAGCA GGAGCGCAGA CGCCCCCGCG
         AAGTAACCCG ATCCGTAGAA GAAGTCTCAC TTCAAGTCGT CCTCGCGTCT GCGGGGGCGC

Y  Q  Q    G  Q  N  Q    L  Y  N    E  L  N    L  G  R  R    E  E  Y
    1621 TACCAGCAGG GCCAGAACCA GCTCTATAAC GAGCTCAATC TAGGACGAAG AGAGGAGTAC
         ATGGTCGTCC CGGTCTTGGT CGAGATATTG CTCGAGTTAG ATCCTGCTTC TCTCCTCATG

D  V  L    D  K  R  R    G  R  D    P  E  M    G  G  K  P    R  R  K
    1681 GATGTTTTGG ACAAGAGACG TGGCCGGGAC CCTGAGATGG GGGGAAAGCC GAGAAGGAAG
         CTACAAAACC TGTTCTCTGC ACCGGCCCTG GGACTCTACC CCCCTTTCGG CTCTTCCTTC

N  P  Q    E  G  L  Y    N  E  L    Q  K  D    K  M  A  E    A  Y  D
    1741 AACCCTCAGG AAGGCCTGTA CAATGAACTG CAGAAAGATA AGATGGCGGA GGCCTACAGT
         TTGGGAGTCC TTCCGGACAT GTTACTTGAC GTCTTTCTAT TCTACCGCCT CCGGATGTCA

E  I  G    M  K  G  E    R  R  R    G  K  G    H  D  G  L    Y  Q  G
    1801 GAGATTGGGA TGAAAGGCGA GCGCCGGAGG GGCAAGGGGC ACGATGGCCT TTACCAGGGT
         CTCTAACCCT ACTTTCCGCT CGCGGCCTCC CCGTTCCCCG TGCTACCGGA AATGGTCCCA

L  S  T    A  T  K  D    T  Y  D    A  L  H    M  Q  A  L    P  P  R
    1861 CTCAGTACAG CCACCAAGGA CACCTACGAC GCCCTTCACA TGCAGGCCCT GCCCCCTCGC
         GAGTCATGTC GGTGGTTCCT GTGGATGCTG CGGGAAGTGT ACGTCCGGGA CGGGGGAGCG

NotI
              ~~~~~~~~~
    1921 TAAGCGGCCG C
         ATTCGCCGGC G
```

FIG. 1C

IN VITRO PRODUCTION OF IFNγ

IVS OF 2/8/00    ELISA: 2/16/00    FILE: CD19>JD#8 OF 12/6/99>CD19(FMC63)pMG^pac
FORMAT:    1.0 x 10$^6$ EACH OF RESPONDERS OR STIMULATORS/WELL IN 2 ml FINAL, 24 WELL PLATE, 72 hr CULTURE.
RESPONDERS:    JD#8 OF 12/6/99 - CD19 CLONES: B6 (8+,W+,Fc-) AND C1 (8+,W+,Fc-).
STIMULATORS:    STIMULATORS (IRRAD. TO 8000 RADS): K562$_x$, DAUDI$_x$, 1873-CRL$_x$, JM-1$_x$, DHL-4$_x$, PARSONS LCL$_x$, SUP-B15$_x$, IONA/PMA, MEDIA.

UNITS[1] = EXTRAPOLATED ABOVE HIGHEST STANDARD

| SAMPLES | DILN PLATED | GM-CSF (pg/ml) | DILN PLATED | TNF□ (pg/ml) | DILN PLATED | IL-2 (pg/ml) | DILN PLATED | IFNγ (pg/ml) |
|---|---|---|---|---|---|---|---|---|
| 1. B6/K562$_x$ | NEAT | 0 | NEAT | 0 | NEAT | 0 | NEAT | 25 |
| 2. B6/DAUDI$_x$ | NEAT | 36 | NEAT | 0 | NEAT | 0 | 1:10 | 1362 |
| 3. B6/1873-CRL$_x$ | NEAT | 113 | NEAT | 0 | NEAT | 0 | 1:10 | 967 |
| 4. B6/ JM-1$_x$ | NEAT | 32 | NEAT | 75 | NEAT | 0 | 1:10 | 396 |
| 5. B6/ DHL-4$_x$ | NEAT | 0 | NEAT | 176 | NEAT | 0 | 1:10 | 645 |
| 6. B6/ LCL$_x$ | NEAT | 85 | NEAT | 71 | NEAT | 0 | 1:10 | 1245 |
| 7. B6/ SUP-B15$_x$ | NEAT | 116 | NEAT | 0 | NEAT | 0 | 1:10 | 946 |
| 8. B6/ I/P | 1:10 | 2231 | NEAT | 803 | 1:20 | 37,155 | 1:10 | >10,000 |
| 9. B6/ MEDIA | NEAT | 0 | NEAT | 0 | NEAT | 0 | NEAT | 0 |
| 10. C1/K562$_x$ | NEAT | 0 | NEAT | 0 | NEAT | 34 | NEAT | 0 |
| 11. C1/DAUDI$_x$ | NEAT | 303 | NEAT | 60 | NEAT | 51 | 1:10 | 1679 |
| 12. C1/1873-CRL$_x$ | NEAT | 296 | NEAT | 60 | NEAT | 36 | ND | |
| 13. C1/ JM-1$_x$ | NEAT | 25 | NEAT | 0 | NEAT | 0 | 1:10 | 631 |
| 14. C1 DHL-4$_x$ | NEAT | 69 | NEAT | 0 | NEAT | 0 | 1:10 | 690 |
| 15. C1/ LCL$_x$ | NEAT | 350 | NEAT | 40 | NEAT | 0 | 1:10 | 1483 |
| 16. C1/ SUP-B15$_x$ | NEAT | 338 | NEAT | 64 | NEAT | 0 | 1:10 | 1245 |
| 17. C1/ I/P | NEAT | 301 | 1:10 | 5552 | 1:20 | 29,892 | ND | |
| 18. C1/ MEDIA | NEAT | 0 | NEAT | 0 | NEAT | 0 | NEAT | 0 |
| 19. K562$_x$ | NEAT | 0 | NEAT | 0 | NEAT | 0 | | |
| 20. DAUDI$_x$ | NEAT | 0 | NEAT | 0 | NEAT | 0 | | |
| 21. 1873-CRL$_x$ | NEAT | 0 | NEAT | 73 | NEAT | 0 | | |
| 22. JM-1$_x$ | NEAT | 0 | NEAT | 0 | NEAT | 0 | | |
| 23. DHL-4$_x$ | NEAT | 0 | NEAT | 0 | NEAT | 0 | | |
| 24. LCL$_x$ | NEAT | 0 | NEAT | 0 | NEAT | 0 | | |
| 25. SUP-B15$_x$ | NEAT | 0 | NEAT | 43 | NEAT | 0 | | |
| 26. I/P | NEAT | 0 | NEAT | 0 | NEAT | 0 | | |
| 27. MEDIA | | | | | | | | |

FIG. 4

CD19-SPECIFIC CHIMERIC T CELL RECEPTOR

CROSS-REFERENCE TO RELATED APPLICATION

This application is a national stage filing under 35 U.S.C. §371 of international application No. PCT/US01/42997, filed Nov. 7, 2001, which claims priority under 35 U.S.C. §119(e) to U.S. Provisional Application Ser. No. 60/246,117, filed Nov. 7,2000, the disclosure of which is incorporated by reference.

BACKGROUND OF THE INVENTION

This invention relates to the field of genetically engineered, redirected immune cells and to the field of cellular immunotherapy of B-cell malignancies, B-cell lymphoproliferative syndromes and B-cell mediated autoimmune diseases. The publications and other materials used herein to illuminate the background of the invention or provide additional details respecting the practice are incorporated by reference.

Approximately half of all hematopoietic stem cell transplantation (HSC) procedures performed in the United States are for the treatment of hematologic malignancy [1]. The initial obstacles for successful HSC transplantation were in large part due to inadequate treatment modalities for ameliorating regimen-related toxicities and for controlling opportunistic infections and graft-versus-host disease (GVHD) [2-5]. As supportive care measures have improved over the last decade, post-transplant disease relapse has emerged as the major impediment to improving the outcome of this patient population [6-10]. The inability of maximally intensive preparative regimens combined with immunologic graft-versus-tumor reactivity to eradicate minimal residual disease is the mechanism of treatment failure in allogeneic transplantation while, in the autologous setting, tumor contamination of the stem cell graft can also contribute to post-transplant relapse [11]. Targeting minimal residual disease early after transplantation is one strategy to consolidate the tumor cytoreduction achieved with myeloablative preparative regimens and purge, in vivo, malignant cells transferred with autologous stem cell grafts. The utility of therapeutic modalities for targeting minimal residual disease shortly following stem cell rescue is dependent on both a limited spectrum of toxicity and the susceptibility of residual tumor cells to the modality's antitumor effector mechanism(s). The successful elimination of persistent minimal residual disease should not only have a major impact on the outcome of transplantation for hematologic malignancy utilizing current myeloablative preparative regimens but may also provide opportunities to decrease the intensity of these regimens and their attendant toxicities.

The prognosis for patients with bcr-abl positive Acute Lymphoblastic Leukemia (ALL) treated with chemotherapy is poor and allogeneic transplantation has offered a curative option for many patients when an appropriate donor was available. For example at the City of Hope, 76 patients with bcr-abl positive ALL were treated with allogeneic Bone Marrow Transplantation (BMT) from a HLA matched donor. Of these patients, 26 were in first remission, 35 were transplanted after first remission. The two year probability of disease free survival was 68% with a 10% relapse rate in those patients transplanted in first remission whereas for those patients transplanted after first remission, the disease-free survival and relapse rate were 36% and 38%, respectively [12]. Post-transplant Polymerase Chain Reaction (PCR) screening of blood and marrow for bcr-abl transcript is under evaluation as a molecular screening tool for identifying early those transplant recipients at high risk for later development of overt relapse [13,14]. Patients for whom detectable p190 transcript was detected following BMT had a 6.7 higher incidence of overt relapse than PCR negative patients. The median time from the development of a positive signal to morphologic relapse was 80-90 days in these patients. The identification of patients in the earliest phases of post-transplant relapse affords the opportunity for making therapeutic interventions when tumor burden is low and potentially most amenable to salvage therapy.

Recent advances in the field of immunology have elucidated many of the molecular underpinnings of immune system regulation and have provided novel opportunities for therapeutic immune system manipulation, including tumor immunotherapy. Evidence supporting the potential of immune-mediated eradication of residual tumor cells following allogeneic transplantation can be inferred by comparing the disparate relapse rates between recipients of syngeneic and non-T cell depleted matched sibling transplants. Patients with chronic myelogenous leukemia in chronic phase (CML-CP), acute myelogenous leukemia in first complete remission ($1^{st}$ CR), and acute lymphoblastic leukemia in $1^{st}$ CR who received a marrow transplant from a syngeneic donor had an actuarial probability of relapse at 3 years of 45%, 49%, and 41%, respectively, whereas the rates for recipients of a non-T depleted marrow transplant from an HLA identical sibling for the same diseases were 12%, 20%, and 24%, respectively [15-17]. The reduction of relapse rates following allogeneic bone marrow transplantation has been most significant in patients who develop acute and/or chronic GVHD. Currently, efforts are focused on developing strategies to selectively augment the graft-versus-leukemia (GVL) response in order to reduce post-transplant relapse rates without the attendant toxicities of augmented GVHD.

Studies in animal models have established that donor MHC-restricted $CD8^+$ and $CD4^+$ $\alpha/\beta^+$ T cells specific for minor histocompatibility antigens encoded by polymorphic genes that differ between the donor and recipient are the principle mediators of acute GVHD and GVL [18-21]. Recently, patients with CML in chronic phase who relapse after allogeneic BMT have been identified as a patient population for whom the infusion of donor lymphocytes (DLI) successfully promotes a GVL effect [22,23]. Complete response rates of approximately 75% are achieved with DLI cell doses in the range of $0.25$-$12.3\times10^8$ mononuclear cells/kg [24]. Although the antitumor activity of donor lymphocyte infusion underscores the potential of cellular immunotherapy for CML, the clinical benefit of DLI has not been generalizable to all forms of hematologic malignancy. Relapsed ALL is much less responsive to DLI with a reported CR rate of less than 20%; when tumor responses are observed, they are typically associated with significant GVHD morbidity and mortality [25]. In order to increase the therapeutic ratio of DLI, genetic modification of donor lymphocytes to express a suicide gene is being evaluated as a strategy to permit the in vivo ablation of donor lymphocytes should toxicity from GVHD warrant this maneuver [26,27]. Alternately, efforts are underway to identify genes encoding minor histocompatibility antigens (mHA's) with restricted hematopoietic expression that elicit donor antigen-specific T cell responses. The isolation, ex vivo expansion, and re-infusion of donor-derived clones specific for these mHA's has the potential of selectively augmenting GVL following allogeneic bone marrow transplantation [28-30].

Non-transformed B-cells and malignant B-cells express an array of cell-surface molecules that define their lineage commitment and stage of maturation. These were identified initially by murine monoclonal antibodies and more recently by molecular genetic techniques. Expression of several of these cell-surface molecules is highly restricted to B-cells and their malignant counterparts. CD20 is a clinically useful cell-surface target for B-cell lymphoma immunotherapy with anti-CD20 monoclonal antibodies. This 33-kDa protein has structural features consistent with its ability to function as a calcium ion channel and is expressed on normal pre-B and mature B cells, but not hematopoietic stem cells nor plasma cells [31-33]. CD20 does not modulate nor does it shed from the cell surface [34]. In vitro studies have demonstrated that CD20 crosslinking by anti-CD20 monoclonal antibodies can trigger apoptosis of lymphoma cells [35,36]. Clinical trials evaluating the antitumor activity of chimeric anti-CD20 antibody IDEC-C2B8 (Rituximab) in patients with relapsed follicular lymphoma have documented tumor responses in nearly half the patients treated, although the clinical effect is usually transient [37-40]. Despite the prolonged ablation of normal CD20$^+$ B-cells, patients receiving Rituximab have not manifested complications attributable to B-cell lymphopenia [41]. Radioimmunotherapy with $^{131}$I-conjugated and $^{90}$Y-conjugated anti-CD20 antibodies also has shown promising clinical activity in patients with relapsed/refractory high-grade Non-Hodgkins Lymphoma but hematopoietic toxicities from radiation have been significant, often requiring stem cell support [42].

Unlike CD20, CD19 is expressed on all human B-cells beginning from the initial commitment of stem cells to the B lineage and persisting until terminal differentiation into plasma cells [43]. CD19 is a type I transmembrane protein that associates with the complement 2 (CD21), TAPA-1, and Leu13 antigens forming a B-cell signal transduction complex. This complex participates in the regulation of B-cell proliferation [44]. Although CD19 does not shed from the cell surface, it does internalize [45]. Accordingly, targeting CD19 with monoclonal antibodies conjugated with toxin molecules is currently being investigated as a strategy to specifically deliver cytotoxic agents to the intracellular compartment of malignant B-cells [46-48]. Anti-CD19 antibody conjugated to blocked ricin and poke-weed antiviral protein (PAP) dramatically increase specificity and potency of leukemia cell killing both in ex vivo bone marrow purging procedures and when administered to NOD-SCID animals inoculated with CD19$^+$ leukemia cells [49]. In vitro leukemia progenitor cell assays have provided evidence that the small percentage of leukemic blasts with the capacity for self-renewal express CD19 on their cell surface. This conclusion was derived from the observations that leukemic progenitor activity is observed exclusively in fresh marrow samples sorted for CD19 positive cells and is not observed in the CD19 negative cell population [50]. Additionally B43-PAP treatment of relapsed leukemic marrow specimens ablates progenitor cell activity while a PAP conjugated antibody with an irrelevant specificity had no such activity [51]. Systemic administration of the CD19-specific immunotoxin B43-PAP is currently undergoing investigation in phase I/II clinical trials in patients with high risk pre-B ALL [52].

Despite the antitumor activity of monoclonal anti-CD20 and anti-CD19 antibody therapy observed in clinical trials, the high rate of relapse in these patients underscores the limited capacity of current antibody-based immunotherapy to eliminate all tumor cells [53]. In contrast, the adoptive transfer of tumor-specific T cells can result in complete tumor eradication in animal models and a limited number of clinical settings [54,55]. The ability of transferred T cells to directly recognize and lyse tumor targets, produce cytokines that recruit and activate antigen non-specific antitumor effector cells, migrate into tumor masses, and proliferate following tumor recognition all contribute to the immunologic clearance of tumor by T cells [56]. Expression-cloning technologies have recently permitted the genetic identification of a growing number of genes expressed by human tumors to which T cell responses have been isolated [57,58]. To date leukemia and lymphoma-specific antigens have not been identified that are both broadly expressed by malignant B-cells and elicit T cell responses. Consequently, preclinical and clinical investigation has focused on combining antibody targeting of tumors with T cell effector mechanisms by constructing bispecific antibodies consisting of CD20 or CD19 binding sites and a binding site for a cell-surface CD3 complex epitope. Such bispecific antibodies can co-localize leukemia and lymphoma targets with activated T cells resulting in target cell lysis in vitro [59-61]. The in vivo antitumor activity of such bispecific antibodies has been limited, however, both in animal models as well as in clinical practice [62]. The discrepancy between in vitro activity and in vivo effect likely reflects the inherent limitations in antibody immunotherapy compounded by the obstacles associated with engaging T cells and tumor cells via a soluble linker in a manner that yields a persistent and functional cellular immune response [63].

The safety of adoptively transferring antigen-specific CTL clones in humans was originally examined in bone marrow transplant patients who received donor-derived CMV-specific T cells [56]. Previous studies have demonstrated that the reconstitution of endogenous CMV-specific T cell responses following allogeneic bone marrow transplantation (BMT) correlates with protection from the development of severe CMV disease [64]. In an effort to reconstitute deficient CMV immunity following BMT, CD8$^+$ CMV-specific CTL clones were generated from CMV seropositive HLA-matched sibling donors, expanded, and infused into sibling BMT recipients at risk for developing CMV disease. Fourteen patients were treated with four weekly escalating doses of these CMV-specific CTL clones to a maximum cell dose of $10^9$ cells/m$^2$ without any attendant toxicity [65]. Peripheral blood samples obtained from recipients of adoptively transferred T cell clones were evaluated for in vivo persistence of transferred cells. The recoverable CMV-specific CTL activity increased after each successive infusion of CTL clones, and persisted at least 12 weeks after the last infusion. However, long term persistence of CD8$^+$ clones without a concurrent CD4$^+$ helper response was not observed. No patients developed CMV viremia or disease. These results demonstrate that ex-vivo expanded CMV-specific CTL clones can be safely transferred to BMT recipients and can persist in vivo as functional effector cells that may provide protection from the development of CMV disease.

A complication of bone marrow transplantation, particularly when marrow is depleted of T cells, is the development of EBV-associated lymphoproliferative disease [66]. This rapidly progressive proliferation of EBV-transformed B-cells mimics immunoblastic lymphoma and is a consequence of deficient EBV-specific T cell immunity in individuals harboring latent virus or immunologically naive individuals receiving a virus inoculum with their marrow graft. Clinical trials by Rooney et al. have demonstrated that adoptively transferred ex-vivo expanded donor-derived EBV-specific T cell lines can protect patients at high risk for development of this complication as well as mediate the eradication of clinically evident EBV-transformed B cells [54]. No significant toxicities were observed in the forty-one children treated with cell doses in the range of $4 \times 10^7$ to $1.2 \times 10^8$ cells/m$^2$.

Genetic modification of T cells used in clinical trials has been utilized to mark cells for in vivo tracking and to endow T cells with novel functional properties. Retroviral vectors have been used most extensively for this purpose due to their relatively high transduction efficiency and low in vitro toxicity to T cells [67]. These vectors, however, are time consuming and expensive to prepare as clinical grade material and must be meticulously screened for the absence of replication competent viral mutants [68]. Rooney et al. transduced EBV-reactive T cell lines with the NeoR gene to facilitate assessment of cell persistence in vivo by PCR specific for this marker gene [69]. Riddell et al. have conducted a Phase I trial to augment HIV-specific immunity in HIV seropositive individuals by adoptive transfer using HIV-specific $CD8^+$ CTL clones [70]. These clones were transduced with the retroviral vector tgLS$^+$HyTK which directs the synthesis of a bifunctional fusion protein incorporating hygromycin phosphotransferase and herpes virus thymidine kinase (HSV-TK) permitting in vitro selection with hygromycin and potential in vivo ablation of transferred cells with gancyclovir. Six HIV infected patients were treated with a series of four escalating cell dose infusions without toxicities, with a maximum cell dose of $5\times10^9$ cells/m$^2$ [70].

As an alternate to viral gene therapy vectors, Nabel et al. used plasmid DNA encoding an expression cassette for an anti-HIV gene in a Phase I clinical trial. Plasmid DNA was introduced into T cells by particle bombardment with a gene gun [71]. Genetically modified T cells were expanded and infused back into HIV-infected study subjects. Although this study demonstrated the feasibility of using a non-viral genetic modification strategy for primary human T cells, one limitation of this approach is the episomal propagation of the plasmid vector in T cells. Unlike chromosomally integrated transferred DNA, episomal propagation of plasmid DNA carries the risk of loss of transferred genetic material with cell replication and of repetitive random chromosomal integration events.

Chimeric antigen receptors engineered to consist of an extracellular single chain antibody (scFvFc) fused to the intracellular signaling domain of the T cell antigen receptor complex zeta chain (ζ) have the ability, when expressed in T cells, to redirect antigen recognition based on the monoclonal antibody's specificity [72]. The design of scFvFc:ζ receptors with target specificities for tumor cell-surface epitopes is a conceptually attractive strategy to generate antitumor immune effector cells for adoptive therapy as it does not rely on pre-existing anti-tumor immunity. These receptors are "universal" in that they bind antigen in a MHC independent fashion, thus, one receptor construct can be used to treat a population of patients with antigen positive tumors. Several constructs for targeting human tumors have been described in the literature including receptors with specificities for Her2/Neu, CEA, ERRB-2, CD44v6, and epitopes selectively expressed on renal cell carcinoma [73-77]. These epitopes all share the common characteristic of being cell-surface moieties accessible to scFv binding by the chimeric T cell receptor. In vitro studies have demonstrated that both $CD4^+$ and $CD8^+$ T cell effector functions can be triggered via these receptors. Moreover, animal models have demonstrated the capacity of adoptively transferred scFvFc:ζ expressing T cells to eradicate established tumors [78]. The function of primary human T cells expressing tumor-specific scFvFc:ζ receptors have been evaluated in vitro; these cells specifically lyse tumor targets and secrete an array of pro-inflammatory cytokines including IL-2, TNF, IFN-γ, and GM-CSF [79]. Phase I pilot adoptive therapy studies are underway utilizing autologous scFvFc:ζ-expressing T cells specific for HIV gp120 in HIV infected individuals and autologous scFvFc:ζ-expressing T cells with specificity for TAG-72 expressed on a variety of adenocarcinomas including breast and colorectal adenocarcinoma.

Investigators at City of Hope have engineered a CD20-specific scFvFc:ζ receptor construct for the purpose of targeting CD20+ B-cell malignancy [80]. Preclinical laboratory studies have demonstrated the feasibility of isolating and expanding from healthy individuals and lymphoma patients CD8+ CTL clones that contain a single copy of unrearranged chromosomally integrated vector DNA and express the CD20-specific scFvFc:zζ receptor [81]. To accomplish this, purified linear plasmid DNA containing the chimeric receptor sequence under the transcriptional control of the CMV immediate/early promoter and the NeoR gene under the transcriptional control of the SV40 early promoter was introduced into activated human peripheral blood mononuclear cells by exposure of cells and DNA to a brief electrical current, a procedure called electroporation [82]. Utilizing selection, cloning, and expansion methods currently employed in FDA-approved clinical trials at the FHCRC, gene modified CD8+ CTL clones with CD20-specific cytolytic activity have been generated from each of six healthy volunteers in 15 separate electroporation procedures [81]. These clones when co-cultured with a panel of human CD20+ lymphoma cell lines proliferate, specifically lyse target cells, and are stimulated to produce cytokines.

It is desired to develop additional redirected immune cells and, in a preferred embodiment, redirected T cells, for treating B-cell malignancies and B-cell mediated autoimmune disease.

SUMMARY OF THE INVENTION

In one aspect, the present invention provides genetically engineered T cells which express and bear on the cell surface membrane a CD19-specific chimeric T cell receptor (referred to herein as "CD19R") having an intracellular signaling domain, a transmembrane domain (TM) and a CD19-specific extracellular domain (also referred to herein as "CD19-specific T cells"). The present invention also provides the CD19-specific chimeric T cell receptors, DNA constructs encoding the receptors, and plasmid expression vectors containing the constructs in proper orientation for expression.

In a second aspect, the present invention provides a method of treating a $CD19^+$ malignancy in a mammal which comprises administering CD19-specific T cells to the mammal in a therapeutically effective amount. In one embodiment, $CD8^+$ CD19-specific T cells are administered, preferably with $CD4^+$ CD19-specific T cells. In a second embodiment, $CD4^+$ CD19-specific T cells are administered to a mammal, preferably with $CD8^+$ cytotoxic lymphocytes which do not express the CD19-specific chimeric receptor of the invention, optionally in combination with $CD8^+$ CD19-specific redirected T cells.

In another aspect, the present invention provides a method of abrogating any untoward B cell function in a mammal which comprises administering to the mammal CD19-specific redirected T cells in a therapeutically effective amount. These untoward B cell functions can include B-cell mediated autoimmune disease (e.g., lupus or rheumatoid arthritis) as well as any unwanted specific immune response to a given antigen.

In another aspect, the present invention provides a method of making and expanding the CD19-specific redirected T cells which comprises transfecting T cells with an expression vector containing a DNA construct encoding the CD19-specific chimeric receptor, then stimulating the cells with CD19+ cells, recombinant CD19, or an antibody to the receptor to cause the cells to proliferate. In one embodiment, the redirected T cells are prepared by electroporation. In a second embodiment, the redirected T cells are prepared by using viral vectors.

In another aspect, the present invention provides a method of targeting Natural Killer (NK) cells which express and bear on the cell surface membrane a CD19-specific chimeric immune receptor having an intracellular signaling domain, a transmembrane domain (TM) and a CD19-specific extracellular domain.

In another aspect, the present invention provides a method of targeting macrophage cells which express and bear on the cell surface membrane a CD19-specific chimeric immune receptor having an intracellular signaling domain, a transmembrane domain (TM) and a CD19-specific extracellular domain.

In another aspect, the present invention provides a method of targeting neutrophils cells which express and bear on the cell surface membrane a CD19-specific chimeric immune receptor having an intracellular signaling domain, a transmembrane domain (TM) and a CD19-specific extracellular domain.

In another aspect, the present invention provides a method of targeting stem cells which express and bear on the cell surface membrane a CD19-specific chimeric immune receptor having an intracellular signaling domain, a transmembrane domain (TM) and a CD19-specific extracellular domain.

In another aspect, the invention provides a CD-19-specific chimeric T-cell receptor comprising an intracellular signalling domain, a transmembrane domain and a CD19-specific extracellular domain.

In one embodiment, the CD19-specific chimeric T cell receptor of the invention comprises scFvFc:ζ, where scFvFc represents the extracellular domain, scFv designates the $V_H$ and $V_L$ chains of a single chain monoclonal antibody to CD19, Fc represents at least part of a constant region of an IgG$_1$, and ζ represents the intracellular signaling domain of the zeta chain of human CD3.

In another embodiment, the CD19-specific chimeric T cell receptor of the invention comprises the scFvFc extracellular domain and the ζ intracellular domain are linked by the transmembrane domain of human CD4.

In another embodiment, the CD19-specific chimeric T cell receptor of the invention comprises amino acids 23-634 of SEQ ID NO:2.

In another aspect, the invention provides a plasmid expression vector containing a DNA construct encoding a chimeric T-cell receptor of the invention in proper orientation for expression.

BRIEF DESCRIPTION OF THE FIGURES

FIGS. 1A-1C show the double-stranded DNA sequence and amino acid sequence for the CD19:zeta chimeric immunoreceptor of the present invention, SEQ ID NO.1 and show the source of the DNA segments found in the chimeric immunoreceptor.

FIG. 4 is a graphical representation showing the antigen-specific cytolytic activity of T-cells expressing the CD19R/scFvFc:ζ chimeric receptor.

DETAILED DESCRIPTION OF THE INVENTION

Figure 2:
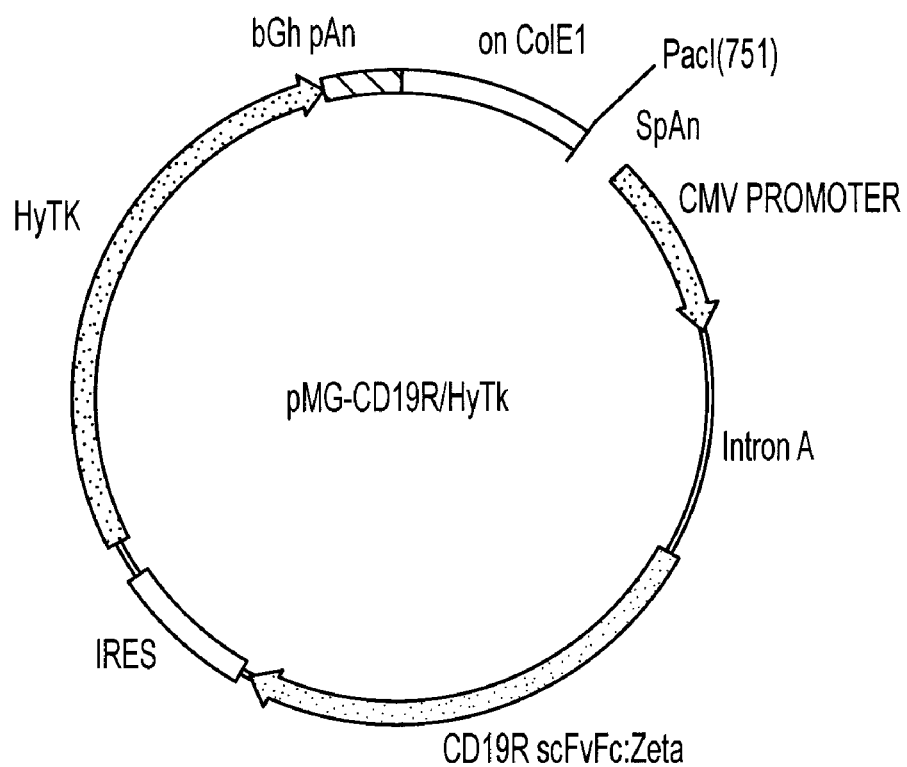
FIG. 2 is a schematic representation of the plasmid pMG-CD19R/HyTK.

The present invention is directed to genetically engineered, redirected T cells and to their use for cellular immunotherapy of B-cell malignancies, Epstein Barr Virus-related lymphoproliferative disorders, and B-cell mediated autoimmune diseases.

In one aspect, the present invention provides genetically engineered T cells which express and bear on the cell surface membrane a CD19-specific chimeric T cell receptor having an intracellular signaling domain, a transmembrane domain and a CD19-specific extracellular domain (referred to herein as CD19-specific T cells). The extracellular domain comprises a CD19-specific receptor. Individual T cells of the invention may be CD4$^+$/CD8$^-$, CD4$^-$/CD8$^+$, CD4$^-$/CD8$^-$ or CD4$^+$/CD8$^+$. The T cells may be a mixed population of CD4$^+$/CD8$^-$ and CD4$^-$/CD8$^+$ cells or a population of a single clone. CD4$^+$ T cells of the invention produce IL-2 when co-cultured in vitro with CD19$^+$ lymphoma cells. CD8$^+$ T cells of the invention lyse CD19$^+$ human lymphoma target cells when co-cultured in vitro with the target cells. The invention further provides the CD19-specific chimeric T cell receptors, DNA constructs encoding the receptors, and plasmid expression vectors containing the constructs in proper orientation for expression.

In a preferred embodiment, CD19-specific redirected T cells express CD19-specific chimeric receptor scFvFc:ζ, where scFv designates the $V_H$ and $V_L$ chains of a single chain monoclonal antibody to CD19, Fc represents at least part of a constant region of a human IgG$_1$, and ζ represents the intracellular signaling domain of the zeta chain of human CD3. The extracellular domain scFvFc and the intracellular domain ζ are linked by a transmembrane domain such as the transmembrane domain of CD4. In other embodiments, the human Fc constant region may be provided by other species of antibody such as IgG$_4$ for example.

In a specific preferred embodiment, a full length scFvFc:ζ cDNA, designated SEQ ID NO.1 or "CD19R:zeta," comprises the human GM-CSF receptor alpha chain leader peptide, FMC63 $V_H$, Gly-Ser linker, FMC63 $V_L$, human IgG$_4$ Fc, human CD4 TM, and human cytoplasmic zeta chain. "Chimeric TCR" means a receptor which is expressed by T cells and which comprises intracellular signaling, transmembrane and extracellular domains, where the extracellular domain is capable of specifically binding in an HLA unrestricted manner an antigen which is not normally bound by a T cell receptor in that manner. Stimulation of the T cells by the antigen under proper conditions results in proliferation (expansion) of the cells and/or production of cytokines (e.g., IL-2) and/or cytolysis.

In another aspect, the present invention provides a method of treating a CD19$^+$ malignancy, lymphoproliferative disease or autoimmune disease mediated in part by B-cells in a mammal which comprises administering CD19-specific redirected T cells to the mammal in a therapeutically effective amount. In one embodiment of this aspect of the invention, a therapeutically effective amount of CD8$^+$ CD19-specific redirected T cells are administered to the mammal. The CD8$^+$ T cells are preferably administered with CD4$^+$ CD19-specific redirected T cells. In a second embodiment of this aspect of the invention, a therapeutically effective amount of $CD4^+$ CD19-specific redirected T cells are administered to the mammal. The $CD4^+$ CD19-specific redirected T cells are preferably administered with $CD8^+$ cytotoxic lymphocytes which express the CD19-specific chimeric receptor of the invention.

In another aspect, the invention provides genetically engineered stem cells which express on their surface membrane a CD19-specific chimeric T cell receptor having an intracellular signaling domain, a transmembrane domain and a CD19-specific extracellular domain.

In another aspect, the invention provides genetically engineered natural killer(NK) cells which express on their surface membrane a CD19-specific chimeric T cell receptor having an intracellular signaling domain, a transmembrane domain and a CD19-specific extracellular domain.

In yet another aspect, the invention provides genetically engineered macrophage which express on their surface membrane a CD19-specific chimeric T cell receptor having an intracellular signaling domain, a transmembrane domain and a CD19-specific extracellular domain.

In another aspect, the present invention provides a method of abrogating any untoward B cell function in a mammal which comprises administering to the mammal CD19-specific redirected T cells in a therapeutically effective amount. Untoward B-cell functions can include B-cell mediated autoimmune disease (e.g., lupus or rheumatoid arthritis) as well as any unwanted specific immune response to a given antigen. For example, CD19-specific redirected T cells can be administered in a method of immunosuppression prior to administering a foreign substance such as a monoclonal antibody or DNA or virus or cell in the situation where any immune response would decrease the effectiveness of the foreign substance.

In another aspect, the present invention provides a method of making and expanding the CD19-specific redirected T cells which comprises transfecting T cells with an expression vector containing a DNA construct encoding the CD19-specific chimeric receptor, then stimulating the cells with $CD19^+$ cells, recombinant CD19, or an antibody to the receptor to cause the cells to proliferate. According to this aspect of the present invention, the method preferably stably transfects and re-directs T cells using electroporation of naked DNA. Alternatively, viral vectors carrying the heterologous genes are used to introduce the genes into T cells. By using naked DNA, the time required to produce redirected T cells can be significantly reduced. "Naked DNA" means DNA encoding a chimeric T cell receptor (TCR) contained in a plasmid expression vector in proper orientation for expression. The electroporation method of this invention produces stable transfectants which express and carry on their surfaces the chimeric TCR (cTCR).

In a preferred embodiment, the T cells are primary human T cells, such as human peripheral blood mononuclear cells (PBMC), which have previously been considered resistant to stable transfection by electroporation of plasmid vectors. Preferred conditions include the use of DNA depleted of endotoxin and electroporation within about 3 days following mitogenic stimulation of T cells. Following transfection, the transfectants are cloned and a clone demonstrating presence of a single integrated unrearranged plasmid and expression of the chimeric receptor is expanded ex vivo. The clone selected for expansion preferably is $CD8^+$ and demonstrates the capacity to specifically recognize and lyse lymphoma target cells which express the target antigen. The clone is expanded by stimulation with IL-2 and preferably another stimulant which is specific for the cTCR.

In another embodiment, the T cells are expressed in immortalized/transformed cells such as the T-cell tumor line TALL101, for example.

The invention is described herein primarily with reference to the specific scFcFv:ζ construct and receptor of SEQ ID Nos: 1 and 2, but the invention is not limited to that specific construct and receptor. Based on the $V_H$ and $V_L$ sequences of the CD19-specific murine IgG1 monoclonal antibody published by Nicholson et al., a scFv sequence was constructed de novo utilizing PCR [83]. The scFv portion can be replaced by any number of different CD19 binding domains, ranging from a minimal peptide binding domain, to a structured CD19 binding domain from a phage library, to antibody like domains using different methods to hold the heavy and light chain together. The arrangement could be multimeric such as a diabody. The secreted form of the antibody forms multimers. It is possible that the T cell receptor variant is also a multimer. The multimers are most likely caused by cross pairing of the variable portion of the light and heavy chains into what has been referred to by Winters as a diabody.

The hinge portion of the construct can have multiple alternatives from being totally deleted, to having the first cysteine maintained, to a proline rather than a serine substitution, to being truncated up to the first cysteine. The Fc portion can be deleted, although there is data to suggest that the receptor preferably extends from the membrane. Any protein which is stable and dimerizes can serve this purpose. One could use just one of the Fc domains, e.g, either the $C_H2$ or $C_H3$ domain.

Alternatives to the CD4 transmembrane domain include the transmembrane CD3 zeta domain, or a cysteine mutated CD3 zeta domain, or other transmembrane domains from other transmembrane signaling proteins such as CD16 and CD8. The CD3 zeta intracellular domain was taken for activation. The intracellular signaling domain of the chimeric receptor of the invention is responsible for activation of at least one of the normal effector functions of the immune cell in which the chimeric receptor has been placed. The term "effector function" refers to a specialized function of a differentiated cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain will be employed, in many cases it will not be necessary to use the entire chain. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal. Examples include the zeta chain of the T cell receptor or any of its homologs (e.g., eta, delta, gamma or epsilon), MB1 chain, B29, Fc RIII and Fc RI and the like. Intracellular signaling portions of other members of the families of activating proteins can be used, such as FcγRIII and FcεRI. See Gross et al. [84], Stancovski et al. [73], Moritz et al. [75], Hwu et al. [85], Weijtens et al. [79], and Hekele et al. [76], for disclosures of cTCR's using these alternative transmembrane and intracellular domains.

Cellular Immunotherapy using Redirected T cells

The strategy of isolating and expanding antigen-specific T cells as a therapeutic intervention for human disease has been validated in clinical trials [86, 65, 87]. Initial studies have evaluated the utility of adoptive T cell therapy with CD8+ cytolytic T cell (CTL) clones specific for cytomegalovirus-encoded antigens as a means of reconstituting deficient viral immunity in the setting of allogeneic bone marrow transplantation and have defined the principles and methodologies for T cell isolation, cloning, expansion and re-infusion [86]. A similar approach has been taken for controlling post-transplant EBV-associated lymphoproliferative disease. EBV-specific donor-derived T cells have the capacity to protect patients at high risk for this complication as well as eradicate clinically evident disease which mimics immunoblastic B cell lymphoma [87]. These studies clearly demonstrate that adoptively transferred ex vivo expanded T cells can mediate antigen-specific effector functions with minimal toxicities and have been facilitated by targeting defined virally-encoded antigens to which T cell donors have established immunity.

The application of adoptive T cell therapy as a treatment modality for human malignancy has been limited by the paucity of molecularly-defined tumor antigens capable of eliciting a T cell response and the difficulty of isolating these T cells from the tumor-bearing host. Consequently, initial cellular immunotherapy trials utilizing autologous antitumor effector cells relied on antigen nonspecific effector cells such as lymphokine activated killer (LAK) cells which had limited efficacy and pronounced toxicities [88, 89]. In an attempt to enhance the tumor-specificity of infused effector cells, IL-2 expanded tumor-infiltrating lymphocytes (TIL) were evaluated [90]. Responses to TIL infusions were sporadic due in part to the heterogeneous population of cells expanded with unpredictable antitumor specificities. Patients with melanoma and renal cell carcinoma however occasionally manifested striking tumor regressions following TIL infusions and tumor-specific MHC-restricted T cell clones have been isolated from these patients. Recently, expression cloning technologies have been developed to identify the genes encoding tumor antigens thereby facilitating the development of recombinant DNA-based vaccine strategies to initiate or augment host antitumor immunity, as well as in vitro culture systems for generating tumor-specific T cells from cancer patients [91]. Clinical trials utilizing autologous tyrosinase-specific CTL for the treatment of melanoma are currently underway.

The inclusion of hematogenous malignancies as targets for T cell therapy is warranted based on the observed graft versus leukemia (GVL) effect observed in the setting of allogeneic BMT and the capacity of donor buffy coat infusions to have anti-leukemic activity [92]. At present, it is clear that T cells present in the marrow graft mount a response to host minor histocompatibility antigens (mHA's) contributing to graft versus host disease and there is increasing evidence that there may be T cell specificities for GVL that are distinct from those of GVHD on the basis of restricted tissue expression of a subset of mHA's [93]. Nevertheless, the susceptibility of malignant B cells to CTL recognition and lysis is well documented [94, 95]. Efforts to target B cell lymphoma with MHC-restricted CTL have focused on the lymphoma clone's idiotype as a tumor-specific antigen. Murine models have demonstrated that CTL responses can be generated to immunoglobulin variable regions and that lymphoma cells process and present these determinants for T cell recognition [96, 97]. Although these strategies are potentially tumor-specific, they are also patient specific thus making large scale application difficult.

Endowing T cells with a desired antigen specificity based on genetic modification with engineered receptor constructs is an attractive strategy since it bypasses the requirement for retrieving antigen-specific T cells from cancer patients and, depending on the type of antigen recognition moiety, allows for targeting tumor cell-surface epitopes not available to endogenous T cell receptors. Studies to define the signaling function of individual components of the TCR-CD3 complex revealed that chimeric molecules with intracellular domains of the CD3 complex's zeta chain coupled to extracellular domains which could be crosslinked by antibodies were capable of triggering biochemical as well as functional activation events in T cell hybridomas [98]. Recent advances in protein engineering have provided methodologies to assemble single chain molecules consisting of antibody variable regions connected by a flexible peptide linker which recapitulate the specificity of the parental antibody [99, 100]. Several groups have now reported on the capacity of chimeric single chain receptors consisting of an extracellular scFv and intracellular zeta domain to re-direct T cell specificity to tumor cells expressing the antibody's target epitope; receptor specificities have included HER2/Neu, and less well characterized epitopes on renal cell and ovarian carcinoma [72, 73, 75, 79, 84, 85]. An idiotype-specific scfv chimeric TCR has been described which recognizes the idiotype-expressing lymphoma cell's surface immunoglobulin as its ligand [101]. Although this approach swaps a low affinity MHC-restricted TCR complex for a high affinity MHC-unrestricted moleculer linked to an isolated member of the CD3 complex, these receptors do activate T cell effector functions in primary human T cells without apparent induction of subsequent anergy or apoptosis [79]. Murine model systems utilizing scFv:ζ transfected CTL demonstrate that tumor elimination only occurs in vivo if both cells and IL-2 are administered, suggesting that in addition to activation of effector function, signaling through the chimeric receptor is sufficient for T cell recycling [76].

Although chimeric receptor re-directed T cell effector function has been documented in the literature for over a decade, the clinical application of this technology for cancer therapy is only now beginning to be applied. Ex vivo expansion of genetically modified T cells to numbers sufficient for re-infusion represents a major impediment for conducting clinical trials. Not only have sufficient cell numbers been difficult to achieve, the retention of effector function following ex vivo expansion has not been routinely documented in the literature.

Treatment of CD19+ Malignancies with CD19-Specific Redirected T Cells

This invention represents the targeting of a B cell malignancy cell-surface epitope with CD19-specific redirected T cells. Malignant B cells are an excellent target for redirected T cells, as B cells can serve as immunostimulatory antigen-presenting cells for T cells [102]. Cytokine production by the CD19-specific scFvFc:ζ expressing Jurkat clones when co-cultured with CD19+ B-cell malignancy does not require the addition of professional antigen presenting cells to culture or pharmacologic delivery of a co-stimulatory signal by the phorbal ester PMA. The function of the CD19R:zeta chimeric immunoreceptor in T cells was first assessed by expressing this scFvFc:ζ construct in primary human T cell clones. Clones secrete cytokines (IFN-γ, TNF-α, and gm-CSF) specifically upon co-culture with human CD19+ leukemia and lymphoma cells. Cytokine production by CD19-specific clones can be blocked in part by the addition to culture of the anti-CD19 specific antibody HIB19. Anti-CD20 antibody Leu-16 does not block cytokine production thereby demonstrating the specificity of the CD19R:zeta chimeric immunoreceptor for CD19 on the tumor cell surface. CD19R:zeta+

CD8+ CTL clones display high levels of cytolytic activity in standard 4-hr chromium release assays against human CD19+ leukemia and lymphoma cell lines cell lines and do not kill other tumor lines that are devoid of the CD19 epitope. These preclinical studies support the anti-tumor activity of adoptive therapy with donor-derived CD19R:zeta-expressing T cell clones in patients that relapse following HLA-matched allogeneic bone marrow transplantation.

We have found that expansion of CD19 specific re-directed CD8+ CTL clones with OKT3 and IL-2 routinely results in the generation of greater than $10^9$ cells over a period of approximately six weeks, and that the clones retain their effector function following expansion, as shown by functional chromium release assay data. Our observation that the plasmid/scFvFc:ζ system can generate transfectants with disrupted plasmid sequence underscores the desirability of cloning transfectants and expanding those clones demonstrating the presence of a single unrearranged integrated plasmid, expression of the chimeric receptor, and the capacity to specifically recognize and lyse CD19+ lymphoma target cells.

CD19 is not tumor-specific and adoptive transfer of cells with this specificity is expected to kill the subset of non-transformed B cells which express CD19. Although CD19 is not expressed by hematopoietic stem cells or mature plasma cells, this cross-reactivity may exacerbate the humoral immunodeficiency of patients receiving chemotherapy and/or radiotherapy. Equipping T cells with a suicide gene such as the herpes virus thymidine kinase gene allows for in vivo ablation of transferred cells following adoptive transfer with pharmacologic doses of gancyclovir and is a strategy for limiting the duration or in vivo persistence of transferred cells [27].

CD19-specific chimeric receptor-expressing T cells of this invention can be used to treat patients with CD19+ B-cell malignancies and B-cell mediated autoimmunie diseases, including for example, acute lymphoblastic leukemia. High relapse rates observed following autologous transplantation for leukemia can be reduced with post-transplant in vivo treatment with adoptively transferred CD19-specific redirected T cells to purge CD19+ leukemic stem cells. CD19-specific redirected T cells can be used to treat lymphoma patients with refractory or recurrent disease. The CD19+ redirected T cells can be administered following myeloablative chemotherapy and stem cell rescue, when tumor burden and normal CD19+ cell burden are at a nadir and when the potential of an immunologic response directed against the scFvFc:ζ protein is minimized.

Patients can be treated by infusing therapeutically effective doses of CD8+ CD19-specific redirected T cells in the range of about $10^6$ to $10^{12}$ or more cells per square meter of body surface (cells/m²). The infusion will be repeated as often and as many times as the patient can tolerate until the desired response is achieved. The appropriate infusion dose and schedule will vary from patient to patient, but can be determined by the treating physician for a particular patient. Typically, initial doses of approximately $10^9$ cells/m² will be infused, escalating to $10^{10}$ or more cells/m². IL-2 can be co-administered to expand infused cells post-infusion. The amount of IL-2 can about $10^3$ to $10^6$ units per kilogram body weight. Alternatively or additionally, an scFvFc:ζ-expressing CD4+ $T_{H1}$ clone can be co-transferred to optimize the survival and in vivo expansion of transferred scFvFc:ζ-expressing CD8+ T cells.

The dosing schedule may be based on Dr. Rosenberg's published work [88-90]or an alternate continuous infusion strategy may be employed. CD19-specific redirected T cells can be administered as a strategy to support CD8+ cells as well as initiate/augment a Delayed Type Hypersensitivity response against CD19+ target cells.

It is known that chimeric immune receptors are capable of activating target-specific lysis by phagocytes, such as neutrophils and NK cells, for example (103). Thus the present invention also contemplates the use of chimeric T-cell receptor DNA to transfect into non-specific immune cells including neutrophils, macrophages and NK cells. Furthermore, the present invention contemplates the use of chimeric T-cell receptor DNA to transfect stem cells prior to stem cell transplantation procedures.

The practice of the present invention employs, unless otherwise indicated, conventional techniques of chemistry, molecular biology, microbiology, recombinant DNA, genetics, immunology, cell biology, cell culture and transgenic biology, which are within the skill of the art. (104-121, e.g.).

EXAMPLES

The present invention is further detailed in the following examples, which are offered by way of illustration and are not intended to limit the invention in any manner, Standard techniques well known in the art or the techniques specifically described below are utilized.

Example 1

Construction of a scFvFc:ζ cDNA Incorporating the FMC63 $V_H$ and $V_L$ Sequences Based on the $V_H$ and $V_L$ sequences of the CD19-specific murine IgG1 monoclonal antibody published by Nicholson et al., a scFv sequence was constructed de novo utilizing PCR [83]. A full length scFvFc:ζ cDNA designated CD19R:zeta was constructed by PCR splice overlap extension and consists of the human GM-CSF receptor alpha chain leader peptide, FMC63 $V_H$, Gly-Ser linker, FMC63 $V_L$, human $IgG_1$ Fc, human CD4 TM, and human cytoplasmic zeta chain. The nucleotide sequence of the construct and the resulting amino acid sequence are set forth in together in FIGS. 1A-C or separately as SEQ ID Nos:1 and 2, respectively.

Figure 3:
FIG. 3 shows Western blot analyses which demonstrate the expression of the CD19R/scFvFc:ζ chimeric receptor.

The CD19-specific scFvFc:ζ receptor protein is expressed in Primary Human T cells. To determine whether the CD19-specific scFvFc:ζ construct could be expressed as an intact chimeric protein, T cells were transfected with the plasmid of Example 1 containing the CD19R. Linearized plasmid was electroporated under optimized conditions and stable transfectants selected by addition of hygromycin to cultures. Referring now to FIG. 3, there are shown the results of Western blot analyses of T-cells transfected with the CD19R receptor in an expression vector of the present invention. Using methods known in the art, whole cell lysates from mock transfectants (cells containing the pMG plasmid without CD19R: MTH7B9), T-cells transfected with CD19R (SG1D12) and T-cells transfected with an anti-CD20 chimeric receptor (AR2H6) were examined. GAM-AP is alakaline phosphatase conjugated goat anti-mouse IgG. This is the second step detection reagent in the western blot that produces a chemiluminescent. Western blot of whole cell lysates with an anti-zeta antibody probe shows both the endogenous zeta fragment and the expected intact 66-kDa chimeric receptor protein is expressed in cells transfected with a chimeric receptor but not in cells transfected with plasmid lacking the DNA constructs of the present invention. Flow cytometric analysis with anti-murine Fab and anti-human Fc specific antibodies further confinmed the cell-surface expression of the CD19R:zeta scFvFc:ζ on T cell transfectants.

Example 2

CD19-Specific Re-Directed Effector Functions of T Cells Expressing the FMC63 Chimeric Immunoreceptor 2(A)-Cytokine Production by Chimeric T-Cells:

Referring now to FIG. 4, the function of the CD19R:zeta chimeric immunoreceptor in T cells was first assessed by expressing this scFvFc:ζ construct in primary human T cell clones. Clones secrete cytokines (IFN-γ, TNF-α, and gm-CSF) specifically upon co-culture with human CD19$^+$ leukemia and lymphoma cells. Using techniques well known in the art and further described herein, chimeric T-cell clones were isolated which expressed the CD19R:zeta chimeric immunoreceptor. FIG. 4 shows the results of incubation of various T-cell clones expressing the recombinant CD19:zeta chimeric immunoreceptor with CD-19 leukemmia cell lines. 1873-CRL is a human CD19+/CD20– ALL cell line purchased from ATCC. DHL-4 is a human CD19+/CD20+ lymphoma cell line. Iona=Ionomycin purchased from Sigma. This chemical is a calcium ionaphore. PMA=Phorbal-12-myristate-13 acetate (Sigma). Iono+PMA when added to T cells maximally activates them for cytokine production. Supernatant of T cells incubated with these chemicals serves as a positive control for maximal cytokine production. The cytokine assays are performed by adding 10$^6$ responsder T cells with the indicated stimulator (if the stimulator is a tumor cell it is added at 2×10$^5$ per 24-well and is irradiated 8K rads). The wells are supplemented with culture media to a final volume of 2 mls and incubated for 72 hrs at which time cell-free supernatants are harvested and assayed by specific ELISA using R+D Systems Kits per the manufactuer's instructions.

Cytokine production by CD19-specific clones can be blocked in part by the addition to culture of the anti-CD19 specific antibody HIB19. Anti-CD20 antibody Leu-16 does not block cytokine production thereby demonstrating the specificity of the CD19R:zeta chimeric immunoreceptor for CD19 on the tumor cell surface.

Figure 5:
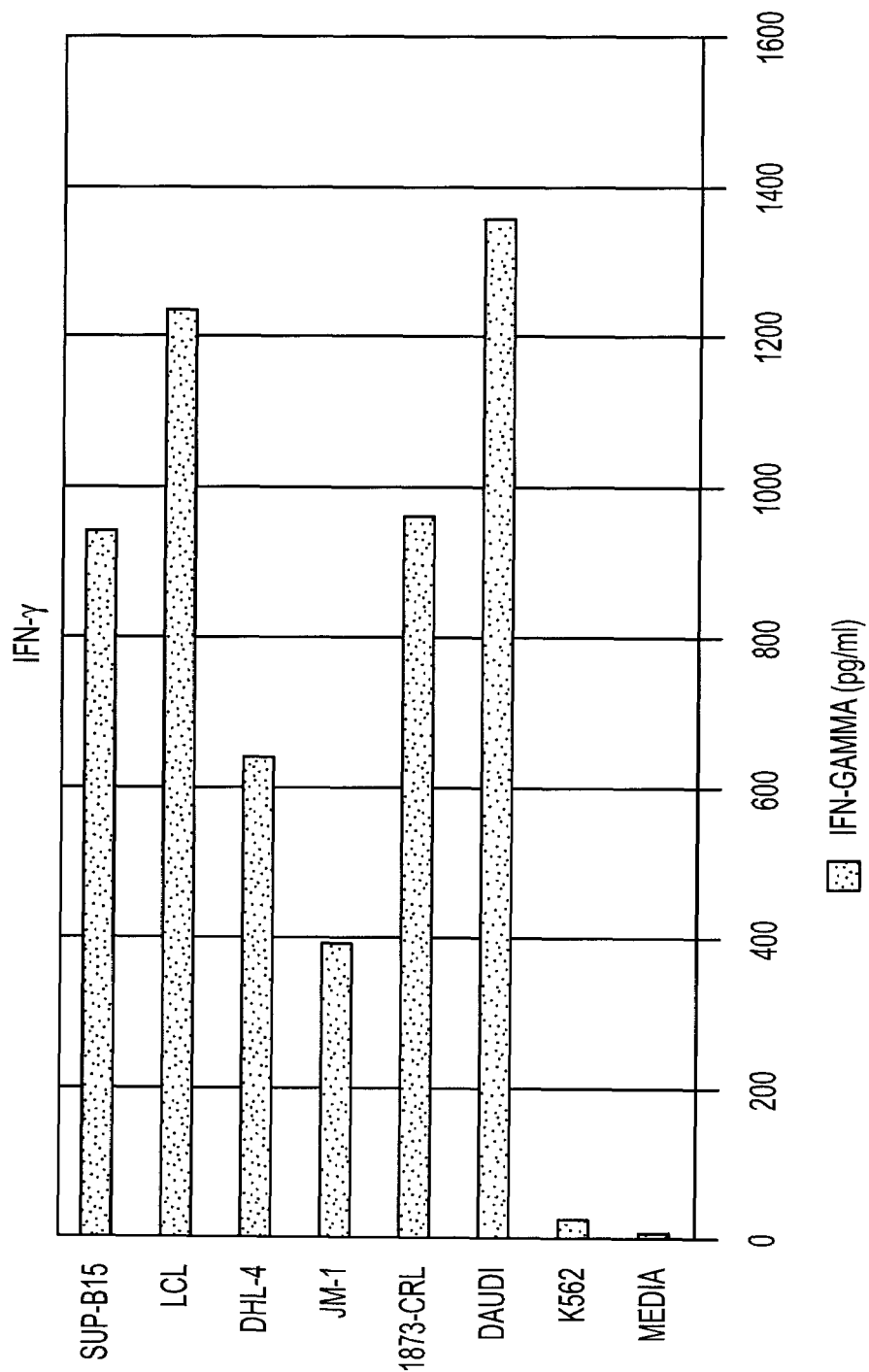
FIG. 5 is a graphical representation of the production of interferon-γ by T cells expressing the CD19R/scFvFc:ζ chimeric receptor that are incubated in the presence of various cell lines expressing CD-19.
Figure 6A:
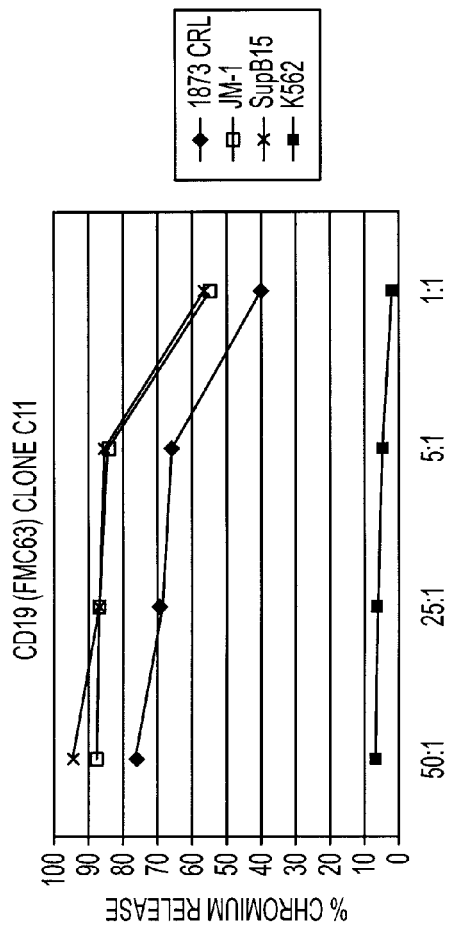
FIGS. 6A-E are graphical representations showing the antigen-specific cytolytic activity of CD19R/scFvFc:ζ chimeric receptor redirected T-cell clones.
Figure 6B:
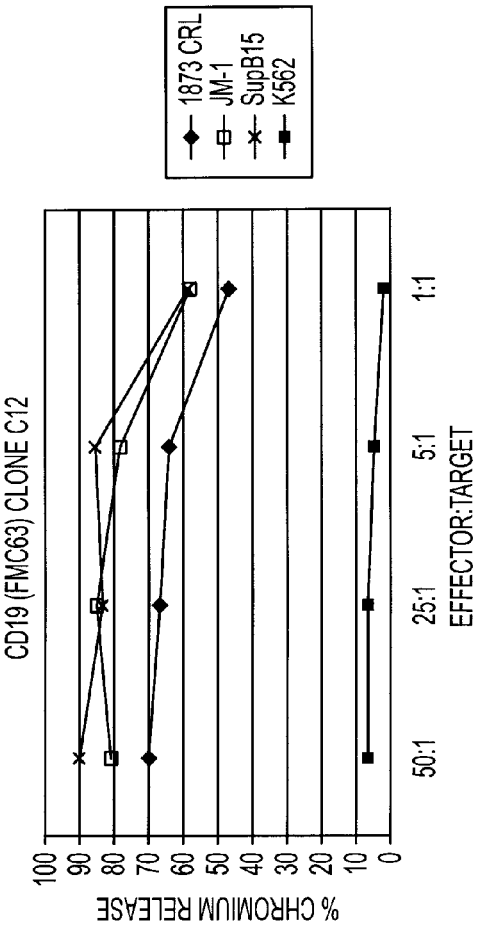
Figure 6C:
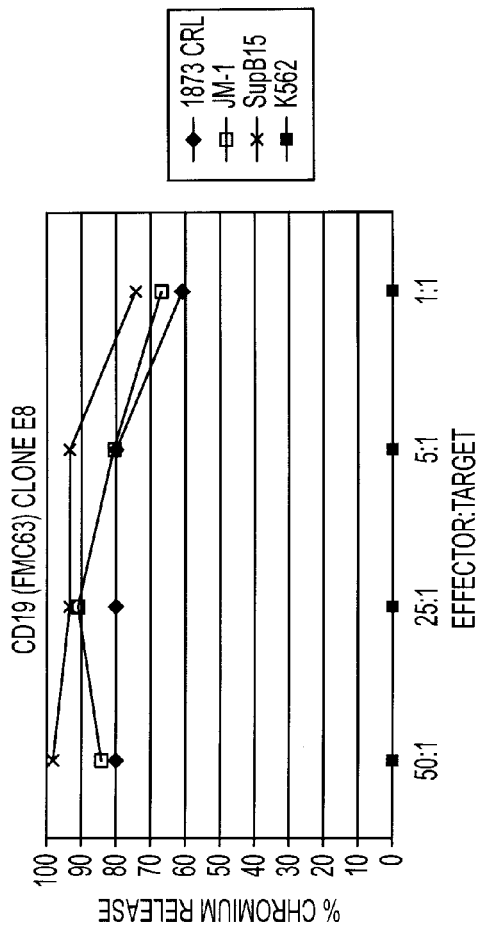
Figure 6D:
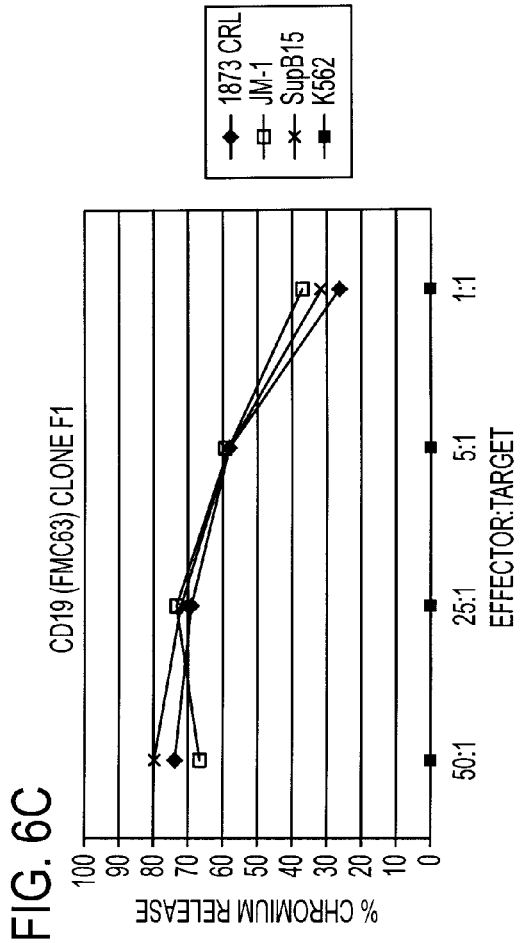
Figure 6E:
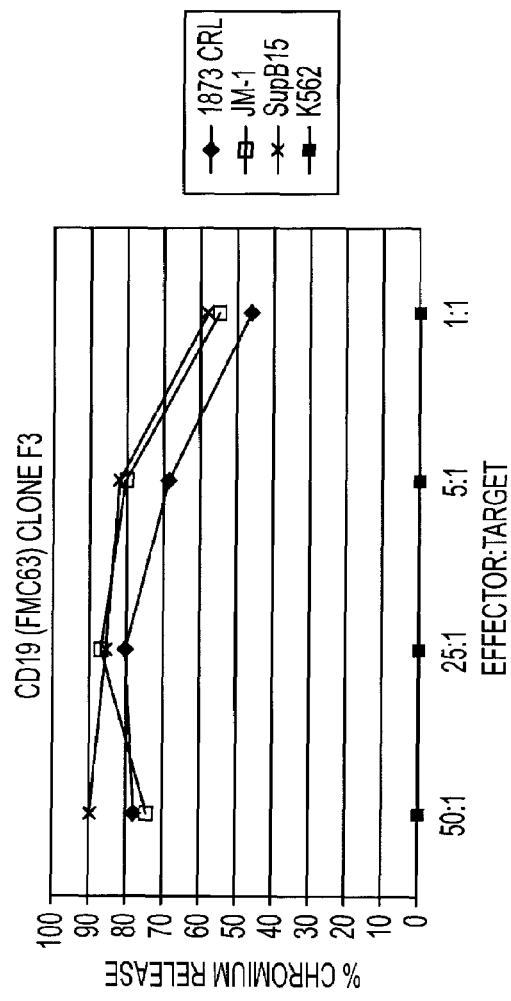

Referring now to FIG. 5, there are shown the results of incubation of the T-cell clone SG1D12 with various cell lines as described, some of which express the CD19 antigen. The graph represents the results of ELISA with antibody specific for IFN-γ. These results demonstrate that T-cells expressing the chimeric receptor release IFN-γ in the presence of CD-19 bearing cells.

(2B)-Antige-Specific Cytolytic Activity of Chimeric T-Cells:

Referring now to FIG. 6, there are shown the results of chromium release assays for 5 different chimeric T-cell clones (C11; C12; E8; F1 and F3). CD19R:zeta$^+$ CD8$^+$ CTL clones display high levels of cytolytic activity in standard 4-hr chromium release assays against human CD19$^+$ leukemia and lymphoma cell lines SUPB15, JM-1 and 1873 and do not kill other tumor lines that are devoid of the CD19 epitope. These preclinical studies support the initiation of clinical investigation to explore the safety and anti-tumor activity of adoptive therapy with donor-derived CD19R:zeta-expressing T cell clones in patients that relapse following HLA-matched allogeneic bone marrow transplantation.

Example 3

Generation and Characterization of T Cell Clones for Therapeutic Use

All T cells administered are TCR α/β$^+$ CD4$^-$CD8$^+$ scFvFc:ζ$^+$T cell clones containing unrearranged chromosomally integrated plasmid DNA. T cells are isolated from the peripheral blood of the transplant recipient's HLA-matched marrow donor. Materials and methods employed to isolate, genetically modify, and expand CD8$^+$ T cell clones from healthy marrow donors are detailed in Examples 4-8. T cell clones genetically modified to express the CD19R:zeta scFvFc:ζ chimeric immunoreceptor and HyTK are selected for:

a. TCRα/β$^+$, CD4$^-$, CD8$^+$ surface phenotype as determined by flow cytometry.
b. Presence of a single copy of chromosomally integrated plasmid vector DNA as evidenced by Southern blot.
c. Expression of the scFvFc:ζ gene product as detected by Western blot.
d. Specific lysis of human CD19$^+$ cell lines in 4-hr chromium release assays.
e. Dependence on exogenous IL-2 for in vitro growth.
f. Mycoplasma, fungal, bacterial sterility and endotoxin levels <5 EU/ml.
g. In vitro sensitivity of clones to ganciclovir.

Example 4

Materials for Isolating, Genetically Modifying and Expanding CD8$^+$ T Cell Clones from Healthy Marrow Donors for Therapeutic Use 1. Culture Media and Media Supplements Culture media used in the studies include RPMI 1640 HEPES (Irvine Scientific, Irvine, Calif.) for all cell cultures. All media is purchased in 0.5 liter bottles and meets current FDA guidelines for use in adoptive immunotherapy studies in humans. Supplements to the culture media include L-glutamine (BioWhittaker, Walkersville, Md.) and fetal calf serum (Hyclone, Logan, Utah) heat inactivated at 56° C. for 30 minutes. All reagents are shipped to CRB-3008, inspected, and stored at –20° C. or 4° C. as appropriate for the reagent.

2. OKT3

Orthoclone OKT3 (Ortho) 1 mg/ml purchased from the City of Hope Pharmacy and aliquoted into sterile cryovials are stored at –20° C. in CRB-3008 until thawed for study subject T cell expansion.

3. Interleukin 2

Pharmaceutical grade recombinant human Interleukin-2 (rhIL-2) (Proleukin) is supplied in vials containing 0.67 mg of lyophilized IL-2 and having a specific activity of 1.5×10$^6$ IU/mg protein. The lyophilized recombinant IL-2 is reconstituted with sterile water for infusion and diluted to a concentration of 5×10$^4$ units/ml. IL-2 is aliquoted into sterile vials and stored at –20° C. in CRB-3008. rhIL-2 for direct patient administration is dispensed per standard practice.

4. Plasmid DNA

The plasmid CD19R/HyTK-pMG containing the CD19-specific scFvFc:ζ cDNA and HyTK cDNA constructs is manufactured under GLP conditions. Ampules containing 100 μg of sterile plasmid DNA in 40 μl of pharmaceutical water. Vector DNA is stored in a –70° C. freezer in CRB-3008.

5. Hygromicin

The mammalian antibiotic hygromycin is used to select genetically modified T cells expressing the HyTK gene. Commercially available hygromycin (Invivogen, San Diego, Calif.) is prepared as a sterile solution of 100 mg/ml active drug and is stored at 4° C. in CRB-3008.

6. EBV-Induced B Cell Lines

Lymphoblastoid cell lines (LCL) are necessary feeder cells for T cell expansion and have been used for this purpose in FDA-approved clinical adoptive therapy trials. An EBV-induced B cell line designated TM-LCL was established from a healthy donor by co-culture of PBMC with supernatants of the B95-8 cell line (American Type Culture Collections) in the presence of cyclosporin A. This cell line is currently being used as an irradiated feeder cell by investigators at the Fred Hutchinson Cancer Research Center (FHCRC) and City of Hope National Medical Center. This cell line has tested negative for adventitious microorganisms as well as EBV production by cord blood transformation assay. Working stocks of TM-LCL have been cyropreserved in CRB-3008 after transfer from Drs. Greenberg and Riddell at the FHCRC. These stocks have been thawed and retested for bacterial, fungal and mycoplasma sterility. TM-LCL feeder cells are irradiated to 8,000 cGy prior to co-culture with T cells.

7. Feeder PBMCs

Peripheral blood mononuclear cells (PBMC) isolated from the study subject's marrow harvested by leukapheresis and transferred to CRB 3008 in a collection bag is used as autologous feeder cells. PBMC from the donor's apheresis product in excess of that quantity needed for establishing T cell cultures is cyropreserved in ampules containing $50 \times 10^6$-$100 \times 10^6$ mononuclear cells in the CRB-3008 liquid nitrogen tank.

Example 5

Generation of CD8+ CTL Clones Genetically Modified to Express the CD19-specific scFvFc:ζ Receptor and HyTK 1. Peripheral Blood Lymphocytes—Collection and Separation Peripheral blood mononuclear cells (PBMC) are obtained from the study subject's designated marrow donor by leukapheresis at the City of Hope National Medical Center. The mononuclear cells are separated from heparinized whole blood by centrifugation over clinical grade Ficoll (Pharmacia, Uppsula, Sweden). PBMC are washed twice in sterile phosphate buffered saline (Irvine Scientific) and suspended in culture media consisting of RPMI, 10% heat inactivated FCS, and 4 mM L-glutamine.

2. Activation of PBMC

T cells present in patient PBMC are polyclonally activated by addition to culture of Orthoclone OKT3 (30 ng/ml). Cell cultures are then incubated in vented T75 tissue culture flasks in the study subject's designated incubator. Twenty-four hours after initiation of culture rhIL-2 is added at 25 U/ml.

3. Genetic Modification of Activated PBMC

Three days after the initiation of culture PBMC are harvested, centrifuged, and resuspended in hypotonic electroporation buffer (Eppendorf) at $20 \times 10^6$ cells/ml. 25 μg of plasmid DNA together with 400 μl of cell suspension are added to a sterile 0.2 cm electroporation cuvette. Each cuvette is subjected to a single electrical pulse of 250V/40μs delivered by the Multiporator (Eppendorf) then incubated for ten minutes at room temperature. Following the RT incubation, cells are harvested from cuvettes, pooled, and resuspended in phenol red-free culture media containing 25 U/ml rhIL-2. Flasks are placed in the patient's designated tissue culture incubator. Three days following electroporation hygromycin is added to cells at a final concentration of 0.2 mg/ml. Electroporated PBMC are cultured for a total of 14 days with media and IL-2 supplementation every 48-hours.

4. Cloning of Hygromycin-Resistant T Cells

The cloning of hygromycin-resistant CD8+ CTL from electroporated OKT3-activated patient PBMC is initiated on day 14 of culture. Cells expressing FvFc product are positively selected for using antibodies to Fab and Fc and/or Protein A-FITC label using techniques well known in the art. Following incubation of electroporated cells with Fab and Fc antibody or Protein A-FITC, cells expressing the FvFc are isolated by immunogenetic beads or colummns or fluorescent activated cell sorting procedures. Viable patient PBMC are added to a mixture of $100 \times 10^6$ cyropreserved irradiated feeder PBMC and $20 \times 10^6$ irradiated TM-LCL in a volume of 200 ml of culture media containing 30 ng/ml OKT3 and 50 U/ml rhIL-2. This mastermix is plated into ten 96-well cloning plates with each well receiving 0.2 ml. Plates are wrapped in aluminum foil to decrease evaporative loss and placed in the patient's designated tissue culture incubator. On day 19 of culture each well receives hygromycin for a final concentration of 0.2 mg/ml. Wells are inspected for cellular outgrowth by visualization on an inverted microscope at Day 30 and positive wells are marked for restimulation.

5. Expansion of Hygromycin-Resistant Clones with CD19 Re-Directed Cytotoxicity

The contents of each cloning well with cell growth and cytolytic activity by screening chromium release assay are individually transferred to T25 flasks containing $50 \times 10^6$ irradiated PBMC, $10 \times 10^6$ irradiated LCL, and 30 ng/ml OKT3 in 25 mls of tissue culture media. On days 1, 3, 5, 7, 9, 11, and 13 after restimulation flasks receive 50 U/ml rhIL-2 and 15 mls of fresh media. On day 5 of the stimulation cycle flasks are also supplemented with hygromycin 0.2 mg/ml. Fourteen days after seeding cells are harvested, counted, and restimulated in T75 flasks containing $150 \times 10^6$ irradiated PBMC, $30 \times 10^6$ irradiated TM-LCL and 30 ng/ml OKT3 in 50 mls of tissue culture media. Flasks receive additions to culture of rhIL-2 and hygromycin as outlined above.

6. Characterization of Hygromycin-Resistant CTL Clones a. Cell Surface Phenotype CTL selected for expansion for use in therapy are analyzed by immunofluorescence on a FACSCalibur housed in CRB-3006 using FITC-conjugated monoclonal antibodies WT/31 (αβTCR), Leu 2a (CD8), and OKT4 (CD4) to confirm the requisite phenotype of clones (αβTCR+, CD4−, and CD8+). Criteria for selection of clones for clinical use include uniform TCR αβ+, CD4−, CD8+ as compared to isotype control FITC-conjugated antibody.

b. Chromosomal Integration of Plasmid

A single site of plasmid vector chromosomal integration is confirmed by Southern blot analysis. DNA from genetically modified T cell clones is screened with a DNA probe specific for the plasmid vector. The Hygro-specific DNA probe is the 420 basepair MscI/NaeI restriction fragment isolated from CD19RR/HyTK-pMG. Probe DNA is $^{32}$P labeled using a random primer labeling kit (Boehringer Mannheim, Indianapolis, Ind.). T cell genomic DNA is isolated per standard technique. Ten micrograms of genomic DNA from T cell clones is digested overnight at 37° C. with 40 units of XbaI and HindIII and then electrophoretically separated on a 0.85% agarose gel. DNA is then transferred to nylon filters (BioRad, Hercules, Calif.) using an alkaline capillary transfer method. Filters are hybridized overnight with the HyTK-specific 32P-labeled probe in 0.5 M $Na_2PO_4$, pH 7.2, 7% SDS, containing 10 µg/ml salmon sperm DNA (Sigma) at 65° C. Filters are then washed four times in 40 mM $Na_2PO_4$, pH 7.2, 1% SDS at 65° C. and then visualized using a phospho-imager (Molecular Dynamics, Sunnyvale, Calif.). Criteria for clone selection is a single unique band with the Hygro probe.

c. Expression of the CD19-Specific scFvFc:ζ Receptor

Expression of the CD19R scFvFc:ζ receptor is determined by Western blot procedure in which chimeric receptor protein is detected with an anti-zeta antibody. Whole cell lysates of transfected T cell clones are generated by lysis of $2 \times 10^7$ washed cells in 1 ml of RIPA buffer (PBS, 1% NP40, 0.5% sodium deoxycholate, 0.1% SDS) containing 1 tablet/10 ml Complete Protease Inhibitor Cocktail (Boehringer Mannheim). After an eighty minute incubation on ice, aliquots of centrifuged whole cell lysate supernatant are harvested and boiled in an equal volume of loading buffer under reducing conditions then subjected to SDS-PAGE electrophoresis on a precast 12% acrylamide gel (BioRad). Following transfer to nitrocellulose, membranes are blocked in blotto solution containing 0.07 gm/ml non-fat dried milk for 2 hours. Membranes are washed in T-TBS (0.05% Tween 20 in Tris buffered saline pH 8.0) then incubated with primary mouse anti-human CD3ζ monoclonal antibody 8D3 (Pharmingen, San Diego, Calif.) at a concentration of 1 µg/ml for 2 hours. Following an additional four washes in T-TBS, membranes are incubated with a 1:500 dilution of goat anti-mouse IgG alkaline phosphatase-conjugated secondary antibody for 1 hour. Prior to developing, membranes are rinsed in T-TBS then developed with 30 ml of "AKP" solution (Promega, Madison, Wis.) per the manufacturer's instructions. Criteria for clone selection is the presence of a 66 kDa chimeric zeta band.

d. Cytolytic Specificity for $CD19^+$ Leukemic Cells and Lack of Cytolytic Activity Against Recipient Fibroblasts Acitivity $CD8^+$ cytotoxic T cell clones expressing the CD19R scFvFc:ζ receptor recognize and lyse human $CD19^+$ leukemia target cells following interaction of the chimeric receptor with the cell surface target epitope in a HLA unrestricted fashion. The requirements for target cell CD19 expression and class I MHC independent recognition were confirmed by assaying several $\alpha\beta TCR^+$, $CD8^+$, $CD4^-$, $CD19R^+$ CTL clones against a panel of MHC-mismatched human leukemia cell lines (SupB15, JM-1, and 1873 CRL ) as well as the $CD19^-$ line K562 (a CD19-negative, NK-sensitive target) and recipient fibroblasts. T cell effectors are assayed 12-14 days following stimulation with OKT3. Effectors are harvested, washed, and resuspended in assay media; $2.5 \times 10^5$, $1.25 \times 10^5$, $0.25 \times 10^5$, and $0.05 \times 10^5$ effectors are plated in triplicate at 37° C. for 4 hours with $5 \times 10^3$ target cells in V-bottom microtiter plates (Costar, Cambridge, Mass.). After centrifugation and incubation, 100 µL aliquots of cell-free supernatant is harvested and counted. Percent specific cytolysis is calculated as follows:

$$\frac{(\text{Experimental } ^{51}\text{Cr release}) - (\text{control } ^{51}\text{Cr release})}{(\text{Maximum } ^{51}\text{Cr release}) - (\text{control } ^{51}\text{Cr release})} \times 100$$

Control wells contain target cells incubated in assay media. Maximum $^{51}$Cr release is determined by measuring the $^{51}$Cr content of target cells lysed with 2% SDS. Criteria for clone selection is >50% specific lysis of both neuroblastoma targets at an effector:target ratio of 25:1 and less than 10% specific lysis of K562 and fibroblasts at an E:T ratio of 5:1.

Example 6

Microbiologic Surveillance of T Cell Cultures

Aliquots of media from the T cell cultures are screened by U.S.P. and fungal culture prior to cryopreservation (Stage I Sterility Testing). Cultures with evident contamination are immediately discarded. T cell expansions for re-infusion have U.S.P. and fungal cultures sent 48-hrs prior to use (Stage II Sterility Testing). To detect mycoplasma contamination, aliquots are assayed using the Gen-Probe test kit (San Diego, Calif.) prior to cryopreservation (Stage I) and cultures with mycoplasma contamination discarded. Within 49-hrs of re-infusion cultures are re-screened as detailed above (Stage II). Prior to cell washing on the day of re-infusion Gram stains are conducted on each bag to exclude overt contamination and endotoxin levels determined by LAL are determined on the washed cell product. An endotoxin burden of <5 EU/kg burden of endotoxin is allowed. Washed T cell clones are also cyropreserved in case archival specimens are needed.

Example 7

Quality Control Criteria for Release of Clones for Re-Infusion

The criteria set forth in Table I must be met prior to release of T cells for re-infusion.

TABLE 1

| | Criteria for Release of Clones | |
|---|---|---|
| Test for: | Release Criteria: | Testing Method: |
| Viability of Clinical Preparation | >90% | Trypan blue exclusion |
| Cell-Surface Phenotype | Uniformly TCRα/β$^+$, CD4$^+$, CD8$^+$ | Flow cytometric evaluation with isotype controls. |
| Vector Integration Number | Single band | Southern Blot with Hygro-Specific Probe |
| scFvFc:ζ Expression | 66-kD Band | Western Blot with Human Zeta-Specific Primary Antibody |
| CD19-Specific Anti-Leukemia Cytolytic Activity | >50% Specific Lysis at E:T Ratio of 25:1 Against SUP-B19 and JM-1 and <10% SL against | 4 hr-Chromium Release Assay |

TABLE 1-continued

Criteria for Release of Clones

| Test for: | Release Criteria: | Testing Method: |
|---|---|---|
| | K562 and fibros at an E:T of 5:1. | |
| Sterility | All Stage I U.S.P./fungal cultures neg at 21 days days. Mycoplasma neg at time of cyropreservation and within 48 hrs of each infusion. Endotoxin level <5 E.L/kg in washed cell preparation. Gram stain negative on day of re-infusion. | Bacterial/fungal by routine clinical specimen culture. Mycoplasma by Gene-Probe RIA. Endotoxin by LAL. Gram stain by clinical microbiology lab. |

Example 8

Quantitative PCR For T Cell Persistence In Vivo

The duration of in vivo persistence of scFvFc:$\zeta^+$ CD8$^+$ CTL clones in the circulation is determined by quantitative PCR (Q-PCR) utilizing the recently developed TaqMan fluorogenic 5' nuclease reaction. Q-PCR analysis is performed by the Cellular and Molecular Correlative Core on genomic DNA extracted from study subject PBMC obtained prior to and on days +1 and +7 following each T cell infusion. Following the third infusion PBMC are also sampled on day +14, +21, +51 (Day +100 following stem cell rescue). Should any study subject have detectable gene-modified T cells on day +100, arrangements are made to re-evaluate the patient monthly until the signal is undetectable. Published data from Riddell et al. has determined that adoptively transferred T cells are detected in the peripheral blood of study subjects one day following a cell dose of $5 \times 10^9$ cells/m$^2$ at a frequency of 1-3 cells/100 PBMC, thus the doses of cells for this study will result in a readily detectable signal (70). DNA is extracted from PBMC using the Qiagen QiAmp kit. The primers used to detect the scFvFc:$\zeta$ gene are 5'HcFc (5'-TCTTCCTCTA-CACAGCAAG CTCACCGTGG-3'; SEQ ID NO:3) and 3'HuZeta (5'-GAGGGTTCTTCCTTCTCG GCTTTC-3'; SEQ ID NO:4) and amplify a 360 basepair fragment spanning the Fc-CD4-TM-zeta sequence fusion site. The TaqMan hybridization probe is FAM-5'TTCACTCTGAA GAAGAT-GCCTAGCC3'-TAMRA (SEQ ID NO:5). A standard curve is generated from genomic DNA isolated from a T cell clone with a single copy of integrated plasmid spiked into unmodified T cells at frequencies of $10^{-2}$, $10^{-3}$, $10^{-4}$, $10^{-5}$, and $10^{-6}$. A control primer/probe set specific for the human beta-globin gene is used to generate a standard curve for cell number and permits the calculation of the frequency of genetically modified clone in a PBMC sample. The beta-globin amplimers are as follows: Pco3 (5'-ACACAACTGTGTTCACTAGC-3'; SEQ ID NO:6), GII (5'-GTCTCCTT AAACCTGTCTTG-3'; SEQ ID NO:7) and the Taqman probe is HEX-5'ACCT-GACTCCTGAGG AGAAGTCT3'-TAMRA (SEQ ID NO:8). All patients will have persistence data and immune response data to the scFvFc:$\zeta$ and HyTK genes compared to determine if limited persistence can be attributed to the development of an immune response to gene-modified T cells.

Example 9

Pilot Phase I Study

1. Staging Criteria and Patient Eligibility a. Staging Criteria

Prior to Study Enrollment
    Immunohistopathologically confirmed CD19$^+$ ALL.
    Molecularly confirmed Ph$^+$ ALL (Cohort 2)
    Bone marrow aspirate and biopsy.
    Lumbar puncture.
    CT scan Chest/ABD/Pelvis.

After Study Enrollment
    Donor Leukapheresis
    Study Subject Skin Biopsy to Establish Fibroblast Cell Line b. Patient Eligibility Patient Inclusion Criteria
    Relapsed CD19+ ALL following HLA-matched related donor BMT (Cohort 1).
    History of Ph$^+$ CD19$^+$ ALL for which an HLA-matched allogeneic bone marrow transplant is indicated (Cohort 2).
    Male or female subjects $\geq$12 months of age and $\leq$65 years of age.
    Consenting related donor HLA-phenotypically identical with the patient for HLA-A, and -B and identical for DRB 1 alleles. Matching assessed minimally by serology for Class I and DNA typing for Class II antigens.
    Patients with adequate organ function as measured by:
        Cardiac: Asymptomatic or, if symptomatic, then left ventricular ejection fraction at rest must be $\geq$50% or within normal range for COH.
        Hepatic: SGOT within 5× normal range and total bilirubin <5× normal range.
        Renal: Serum creatinine within 1.5× normal range or creatinine clearance 60 ml/min.
        Pulmonary: DLCO >45% of predicted (corrected for hemoglobin) or within normal range for COH.
    Adequate performance status 70% (Karnofsky-age >18yrs, Lansky $\leq$18yrs of age).
    Written informed consent from patient and donor conforming to COH guidelines obtained from donor and patient or patient & parent/legal guardian age ($\geq$7yrs)
    Life expectancy >8 weeks and absence of co-existing medical/psychological problems which would significantly increase the risk of the transplant procedure and T cell re-infusions based on the judgement of the study chairperson.

Availability of patient for peripheral blood sample drawing for study tests following transplantation as outlined in Appendix C.

Patient Exclusion Criteria

Prior autologous or allogeneic bone marrow or PBSC transplant (Cohort 2).

Patients who cannot complete total body irradiation dose requirements due to prior radiation treatment (Cohort 2).

Female patients who are pregnant or breast feeding.

Positive serology for HIV.

Active infection requiring intravenous treatment with anti-fungal, anti-bacterial or antiviral agents within two weeks prior to conditioning with the exception of coagulase negative staphylococcal line infection (Cohort2).

Failure to understand the basic elements of the protocol and/or the risks/benefits of participating in this phase I study (Children ≧7-yrs as well as parent/legal guardian as determined by performance on a questionnaire administered prior to consent signing).

Donor Selection

Willingness to undergo leukapheresis for PBMC collection.

2. Study Design and Rules for Dose Escalation

The pilot Phase I study is an open-label, nonrandomized study. In this study patients either who suffer a relapse of their CD19$^+$ ALL following BMT (Cohort 1) or who experience a molecular post-transplant relapse of their Ph$^+$ CD19$^+$ ALL receive donor-derived CD19R$^+$HyTK$^+$CD8$^+$ CTL clones. T cell clones are generated from a leukapheresis product obtained from the patient's HLA-matched related marrow donor. For patients enrolled into Cohort 2, clones are cryopreserved until such time that the research participant is diagnosed with a molecular relapse based on a positive and confirmatory PCR result for bcr-abl. Each research participant in each cohort receives a series of three escalating cell dose T cell infusions at two-week intervals beginning as soon as clones are available (typically by the 14th day following the diagnosis of molecular relapse in cohort 2, and as soon as clones are ready in cohort 1). Those research subjects on immunosuppressive medications for GVHD prophylaxis/treatment are first tapered off corticosteroids and have no more than grade 2 AGVHD prior to commencing with T cell administrations. The first cell dose is 1×10$^9$ cells/m$^2$, the second 5×10$^9$ cells/m$^2$, and the third 5×10$^9$ cells/m$^2$ with IL-2. Patients without significant toxicity attributed to the T cell infusions and who have ≦grade 2 GVHD receive low-dose s.c. rhIL-2 for 14 days with the third T cell dose. Patients are evaluated prior to and weekly after the first infusion for a period of two months after which time, patients are evaluated monthly for an additional six months. Peripheral blood is drawn at specific times during the study to assay for the in vivo persistence of the transferred CTL clones and the induction of anti-scFvFc:ζ and HyTK immune responses. Anti-tumor responses are assessed by changes in the molecular tumor burden by serial Q-PCR for their leukemia-specific marker or bcr-abl, and, by standard morphologic, flow cytometric, and chimerism studies for ALL. The patient's primary Hematologist or pediatric oncologist manages the non-study specific aspects of their patient's medical management throughout the duration of the study and indefinitely thereafter.

3. Treatment Plan a. Schedule of Administration of CD19R:zeta$^+$, CD8$^+$ T Cell Clones The phase I pilot study determines the safety and toxicity of intravenously infused donor-derived CD8$^+$ CTL clones genetically modified to express the CD19R scFvFc:ζ chimeric immunoreceptor and the selection/suicide gene HyTK. A series of three escalating cell dose infusions (Table 2) are administered at two-week intervals to research participants who demonstrate a post-transplant molecular relapse. T cell infusions commence at the earliest time of their availability (Cohort 1), or after documentation of a molecular leukemic relapse (Cohort 2) provided that research participants have tapered off steroids and have no more than grade 2 acute graft-versus-host disease. Low-dose subcutaneously administered IL-2 is given after the third T cell infusion to support the in vivo persistence of transferred CTL. IL-2 administration begins 24-hrs following adoptive transfer of T cell clones and continue for 14 days provided that no grade 3-4 toxicity (see below) is observed with the administration of the first two T cell doses and that AGVHD is ≦grade 2.

TABLE 2

CD19R$^+$HyTK$^+$, CD8$^+$ Cytotoxic T Cell Administration Schedule

| Cell Dose | Protocol Day | Cell Dose |
|---|---|---|
| I | 0 | 1 × 10$^9$ cells/m$^2$ BSA |
| II | +14 | 5 × 10$^9$ cells/m$^2$ BSA |
| III | +28 | 5 × 10$^9$ cells/m$^2$ BSA with s.c. IL-2 (5 × 10$^5$ U/m2/dose q 12-hrs) |

Each infusion consists of a composite of up to five T cell clones to achieve the cell dose under study.

Study subjects who have B cell engraftment at the time relapse is detected with CD20$^+$ cells accounting for >10% of lymphocytes in the circulation receive a single dose (250 mg/m$^2$) of Rituximab (chimeric anti-CD20 antibody) one week prior to the first T cell infusion.

On the day of infusion, T cell clones expanded in CRB-3008 are aseptically processed per standard technique on a CS-3000 blood separation device for cell washing and concentrating. Processed cells are resuspended in 100 ml of 0.9% NaCl with 2% human serum albumin in a bag for suitable for clinical re-infusion.

Study subjects are admitted to the GCRC at COHNMC for their T cell infusions and are discharged no sooner than 23 hours following their infusion provided that no toxicities are observed. Otherwise patients remain hospitalized until resolution of any infusion-related toxicity deemed to pose a significant risk to the study subject as an outpatient.

T cells are infused intravenously over 30 minutes through a central line if available, if not an age appropriate sized I.V. catheter is inserted into a peripheral vein. The I.V. tubing does not have a filter to avoid trapping of cells. The infusion bag is gently mixed every 5 minutes during the infusion.

The doctor or his representative is present during the infusion and immediately available for 2 hours following the infusion. Nursing observation and care is employed throughout the patient's hospital stay.

Subjects' oxygen saturation is measured by continuous pulse-oximetry beginning pre-infusion and continuing for at least 2 hrs or until readings return to their pre-infusion baseline.

Subjects experiencing transplant-related toxicities have their infusion schedule delayed until these toxicities have resolved. The specific toxicities warranting delay of T cell infusions include:

(a) Pulmonary: Requirement for supplemental oxygen to keep saturation greater than 95% or presence of radiographic abnormalities on chest x-ray that are progressive; (b) Cardiac: New cardiac arrhythmia not controlled with medical management. Hypotension requiring pressor support; (c) Active Infection: Positive blood cultures for bacteria, fungus, or virus within 48-hours of day 0; (d) Hepatic: Serum total bilirubin, or transaminases more than 5× normal limit; (e) Renal: Serum creatinine >2.0 or if patient requires dialysis; (f) Neurologic: Seizure activity within one week preceding day 0 or clinically detectable encephalopathy or new focal neurologic deficits; (g) Hematologic: Clinically evident bleeding diathesis or hemolysis.

Patients having anti-tumor responses based on bcr-abl Q-PCR but persistent residual disease following the third T cell dose may have additional cell doses ($5 \times 10^9$ cells/m²/dose at 14 day intervals) with IL-2 ($5 \times 10^5$ U/m² q 12-hrs) provided grade 3 or higher toxicity is encountered.

b. Interleukin-2 Administration

Recombinant human IL-2 (rHuIL-2, Proleulin, Chiron, Emeryville, Calif.) resuspended for s.c. injection by standard pharmacy guidelines is administered to study participants provided that (1) no grade 3-4 toxicities are encountered at cell dose levels I-II and (2) GVHD is not more than grade 2 off immunosuppressive medications. Based on previous experience in Seattle administering s.c. IL-2 to melanoma patients receiving adoptive T cell therapy the IL-2 dose is $5 \times 10^5$ U/m² q 12-hrs for 14 days beginning on the day of T cell re-infusion #3.

c. Management of Toxcities and Complications

The management of mild transient symptoms such as have been observed with LAK, TIL, and T cell clone infusions symptoms is as follows. (1) All patients are pre-medicated with 15 mg/kg of acetaminophen p.o. (max. 650 mg.) and diphenhydramine 1 mg/kg I.V. (max dose 50 mg). (2) Fever, chills and temperature elevations >101° F. are managed with additional tylenol as clinically indicated, 10 mg/kg ibuprofen p.o. (max 400 mg) for breakthrough fevers, and 1 mg/kg demerol I.V. for chills (max 50 mg). Additional methods such as cooling blankets are employed for fevers resistant to these measures. All subjects that develop fever or chills have a blood culture drawn. Ceftriaxone 50 mg/kg I.V. (max dose 2 gms) is administered to non-allergic patients who in the opinion of the physician in attendance appear septic; alternate antibiotic choices are used as clinically indicated. (3) Headache is managed with acetaminophen. (4) Nausea and vomiting are treated with diphenhydramine 1 mg/kg I.V. (max 50 mg). (5) Transient hypotension is initially managed by intravenous fluid administration, however, patients with persistent hypotension require transfer to the intensive care unit for definitive medical treatment. (6) Hypoxemia is managed with supplemental oxygen.

Patients receive ganciclovir if grade 3 or 4 treatment-related toxicity is observed. Parentally administered ganciclovir is dosed at 10 mg/kg/day divided every 12 hours. A 14-day course is prescribed but may be extended should symptomatic resolution not be achieved in that time interval. All patients not hospitalized at the time of presenting symptoms are hospitalized for the first 72 hours of ganciclovir therapy for monitoring purposes. If symptoms do not respond to ganciclovir within 72 hours additional immunosuppressive agents including but not limited to corticosteroids and cyclosporin are added at the discretion of the principle investigator.

d. Concomitant Therapy

All standard supportive care measures for patients undergoing experimental therapies are used at the discretion of the patient's City of Hope pediatric oncologist. Active infections occurring after study enrollment are treated according to the standard of care. The following agents are not allowed while on study: systemic cortico-steroids (except as outlined for management of T cell therapy toxicity), immunotherapy (for example—interferons, vaccines, other cellular products), pentoxifylline, or other investigational agents), ganciclovir or any ganciclovir derivatives for non-life threatening herpes virus infections.

4. Toxicities Monitored and Dosage Modifications a. Toxicities to be Monitored

Toxicity criteria for the pilot phase I study is per the NCI Common Toxicity Criteria (CTC) version 2.0 for toxicity and Adverse Event Reporting. A copy of the CTC version 2.0 is downloadable from the CTEP home page (http://ctep.info.nih.gov/l). All CTC guidelines apply to toxicity assessment except serum measurements of total bilirubin, ALT and AST. Due to the frequent and prolonged observed elevations in bilirubin and hepatic transaminases in cancer patients who have recently received chemotherapy, a grade 1 toxicity is an elevation from their pre-T cell infusion base line up to 2.5× that baseline level. Grade 2 hepatic is a >2.5-5× rise from their pre-T cell infusion baseline, a grade 3 toxicity >5-20× rise, and grade 4>20× baseline. Any toxicity reported by research participants while receiving treatment or in follow-up for which there is no specific CTC designation is graded on the following scale: Grade 0- no toxicity, Grade 1- mild toxicity, usually transient, requiring no special treatment and generally not interfering with usual daily activities, Grade 2- moderate toxicity that may be ameliorated by simple therapeutic maneuvers, and impairs usual activities, Grade 3- severe toxicity which requires therapeutic intervention and interrupts usual activities. Hospitalization may be required or may not be required. Grade 4- life-threatening toxicity that requires hospitalization.

b. Criteria for Dose Modification

If a patient develops grade 2 toxicity with dose level I, the second cell dose for that patient remains at T cell dose level I. Only if the maximal toxicity observed with the second infusion is limited to grade 2 will the third and final cell dose be administered. If the first grade 2 toxicity occurs with the second cell dose, the third cell dose is not be accompanied with s.c. IL-2.

c. Criteria for Removal of Patient from Treatment Regimen

If any patient develops grade 3 or higher toxicity or grade 3 or higher GVHD, IL-2 if being administered is stopped. Ganciclovir treatment as outlined above is initiated at the time a grade 3 or higher toxicity is encountered in those patients not receiving IL-2. For those patients receiving IL-2, ganciclovir treatment commences within 48-hours of stopping IL-2 if the encountered toxicity has not decreased to ≦grade 2 in that time interval. A grade 3 IL-2 injection site toxicity is an indication to discontinue IL-2 but not ablate T cells. Immunosuppression for GVHD is instituted in addition to ganciclovir administration in those patients with grade 3 or higher GVHD. Any patient requiring ganciclovir for T cell ablation does not receive further cell doses but continues being monitored per protocol. At the discretion of the principle investigator, corticosteroids and/or other immunosuppressive drugs are added to ganciclovir should a more rapid tempo of resolution of severe toxicities be indicated.

d. Research Participant Premature Discontinuation

Research participants who do not complete the study protocol are considered to have prematurely discontinued the study. The reasons for premature discontinuation (for example, voluntary withdrawal, toxicity, death) are recorded on the case report form. Final study evaluations are completed at the time of discontinuation. Potential reasons for premature discontinuation include: (a)the development of a life-threatening infection; (b) the judgment of the principal investigator that the patient is too ill to continue; (c) patient/family non-compliance with study therapy and/or clinic appointments; (d) pregnancy; (e) voluntary withdrawal—a patient or his/her parents/legal guardians may remove himself/herself from the study at any time without prejudice; (f) significant and rapid progression of neuroblastoma requiring alternative medical, radiation or surgical intervention; (g) grade 3 or 4 toxicity judged to be possibly or probably related to study therapy; and (h) technical difficulties are encountered in the T cell genetic modification, cloning, and expansion procedure precluding the generation of clinical cell doses that meet all Quality Control criteria.

e. Study Closure

The study is discontinued if a grade 4 or higher toxicity is seen in the first two patients at dose level I or if at any time during the protocol an incidence of grade 4 toxicity in study subjects exceeds 50%. Death from tumor progression greater than thirty days from the last T cell infusion is not be scored as a grade V toxicity, nor be scored as an adverse event. The study can be terminated by the principal investigator, the IRB, or the Food and Drug Administration.

5. Study Parameters and Calender (Table 3)

To occur concurrently with the patient's evaluation for disease relapse and prior to commencing with salvage chemotherapy. The specific studies/procedures include:

- Review of pathologic specimens to confirm diagnosis of $CD19^+$ acute lymphoblastic leukemia.
- Review molecular confirmation of Ph-positivity
- Verify inclusion/exclusion criteria by history.
- Administer the educational proctoring to the potential research participant ($\geq$7-yrs of age) and the parent/legal guardian, conduct the post-educational assessment.
- Obtain informed consent for enrollment from patient and donor.
- Obtain EBV and HIV serologies.
- For $Ph^-$ patients in Cohort 1 ship a sample of blood/marrow to Dr. Radich (FHCRC) for generating leukemic clone PCR amplimers.
- Conduct staging studies as outlined above.
- Skin Biopsy from consented research participant for establishing a fibroblast cell line.

(b) Isolation of Peripheral Blood Mononuclear Cells For the Initiation of T Cell Cultures Consented patients with HLA-matched related donors satisfying inclusion/exclusion criteria undergo a leukapheresis procedure at the City of Hope Donor/Apheresis Center. The leukapheresis product is transferred to CRB-3008 to initiate T cell cultures.

(c) Day -7 to -1: Pre-t Cell Infusion Restaging

Conduct restaging studies as outlined above.

Administration of Rituximab if peripheral $CD20^+$ B cells account for more than 10% of circulating mononuclear cells.

(d) Day 0:evaluation immediately Prior to T Cell Infusion

Review of medical status and review of systems

TABLE 3

| | Calender of Specific Evaluations | | | | | | | | | | | | |
|---|---|---|---|---|---|---|---|---|---|---|---|---|---|
| | Screening Visit | Infusion #1 | Day +1 | Day +7 | Infusion #2 Day +14 | Day +15 | Day +21 | Infusion #3 Day +28 | Day +29 | Day +35 | Day +42 | Day +56/70 | Day +100 |
| History and Physical/Lansky Score | X | X | X | X | X | X | X | X | X | X | X | X | X |
| CBC, diff, plt | X | X | X | X | X | X | X | X | X | X | X | X | X |
| Chem | X | X | X | X | X | X | X | X | X | X | X | X | X |
| EBV, HIV Serilogies | X | | | | | | | | | | | | |
| Q-PCR for plasmid Sequence in PBMC | | X | X | X | X | X | X | X | X | X | X | X | X |
| Q-PCR for BCR-ABL | | X | | X | X | | X | X | | X | X | X | X |
| Bone Marrow Evaluation Morphologic/Flow/Chimerism | | X* | | | | | | | | | | X | X |
| Peripheral Blood for Immune Response | | | | | | | | | | | | | X |

*X: May be performed within 72-hrs prior to infusion #1 a. Screening Visit

Physical examination, vital signs, weight, height, body surface area
List of concomitant medications and transfusions
Karnofsky/Lansky performance status (see Table 4)
Complete blood count, differential, platelet count
Chem 18
Blood for protocol-specific (see Table 3)

TABLE 4

Lansky Scale

| | % | |
|---|---|---|
| Able to carry on normal activity; no special care needed | 100 | Fully active |
| | 90 | Minor restriction in physically strenuous play |
| | 80 | Restricted in strenuous play, tires more easily, otherwise active |
| Mild to moderate restriction | 70 | Both greater restrictions of, and less time spent in active play |
| | 60 | Ambulatory up to 50% of time, limited active play with assistance/supervision |
| | 50 | Considerable assistance required for any active play; fully able to engage in quiet play |
| Moderate to severe restriction | 40 | Able to initiate quiet activities |
| | 30 | Needs considerable assistance for quiet activity |
| | 20 | Limited to very passive activity initiated by others (e.g. TV) |
| | 10 | Completely disabled, not even passive play |

(e) 0, +14, +28: Clinical Evaluation During and after T Cell Infusions

Prior to the Infusion:
  Interval History and Physical Exam
  Blood draw for laboratory studies (see Table 3)

During the Infusion:
  Vital signs at time 0, and every 15 minutes during the infusion, continuous pulse oximetery Following the T Cell Infusion:
  Vital Signs hourly for 12 hours
  Oxygen saturation will be monitored for 2 hours following T cell infusions. Values will be recorded prior to initiating the infusion, immediately post-infusion, and 2 hours post-infusion. In addition, values will be recorded every 15 minutes if they fall below 90% until the patient recovers to his/her pre-infusion room-air baseline saturation.
  Events will be managed by standard medical practice.

Prior to Discharge:
  Interval History and Physical Exam
  Blood draw for laboratory studies (see Table 3)
(f) Days +1, +7, +15, +21, +29, +35, +42, +56, +70, +100
  Interval History and Physical Exam
  Blood draw for CBC, diff, plt, and Chem 18
  3 cc/kg pt wt of heparinized (preservative-free heparin 10 U/10 ml) blood sent to CRB-3002 for direct assay of peripheral blood lymphocytes for vector DNA by PCR
    (g) Bone Marrow Aspirate and Biopsy: Days −7–0, +56, +100
    (h) If a research participant is taken off study after receiving T cells, restaging bone marrow evaluation will be evaluated 28 days and 56 days following the last T cell dose administered.

6. Criteria for Evaluation and Endpoint Definitions (a) Criteria for Evaluation

The phase I data obtained at each clinical assessment is outlined in Table 3. The following toxicity and adverse event determination will be made: (a) symptoms and toxicities are evaluated as described above; (b) physical exam and blood chemistry/hematology results; and (c) adverse event reporting (b) Disease Status At each disease assessment outlined in Table 3 the determination of measurable disease is recorded as follows: (1) Q-PCR for leukemic-specific ampliners or bcr-abl and (2) on days +56 and +100 bone marrow studies will be evaluated and responses graded per standard ALL criteria (Table 5).

TABLE 5

Disease Response Criteria

| | |
|---|---|
| Progressive Disease (PD): | >25% Increase in BCR-ABL Transcript By Q-PCR and/or Progression to Overt Relapse |
| Stable Disease (SD): | <25% Increase in BCR-ABL Signal by Q-PCR AND No Progression to Overt Relapse |
| Partial Response (PR): | ≧25% Decrease in BCR-ABL Signal By Q-PCR AND No Evidence of Overt Relapse |
| Complete Response (CR): | Loss of Detectable BCR-ABL Signal and No Evidence of Overt Relapse |

7. Reporting Adverse Events

Any sign, symptom or illness that appears to worsen during the study period regardless of the relationship to the study agent is an adverse event. All adverse events occurring during the study, whether or not attributed to the study agent, that are observed by the Investigator or reported by the patient are recorded on the Case Report Form and are reported as required by the FDA. Attributes include a description, onset and resolution date, duration, maximum severity, assessment of relationship to the study agent or other suspect agent(s), action taken and outcome. Toxicities arising while on study are scored according to a 0-4 scale based on the criteria delineated in the Common Toxicity Criteria (CTC) Version 2.0 (see above). Association or relatedness to the study agent are graded as follows: 1=unrelated, 2=unlikely, 3=possibly, 4=probably, and 5=definitely related.

Serious adverse events occurring during or after completion of therapy are defined as any one of the following: (a) patient death, regardless of cause, occurring within 30 days of study agent administration; (b) life threatening event; (c) prolonged hospitalization or requirement for additional hospitalizations during treatment and monitoring period due to toxicities attributed to study; (d) congenital anomaly in offspring conceived after initiation of study; (e) requirement for significant medical treatment due to toxicities encountered while on study; and (f) overdose of cells infused.

A life-threatening event is defined as having placed the patient, in the view of the Investigator, at immediate risk of death from the adverse event as it occurred. It does not include an adverse event that, had it occurred in a more serious form, might have caused death. All adverse events that do not meet at least one of the above criteria are defined as non-serious. Assessment of the cause of the event has no bearing on the assessment of the event's severity.

Unexpected adverse events are those which: (a) are not previously reported with adoptive T cell therapy and (b) are symptomatically and pathophysiologically related to a known toxicity but differ because of greater severity or specificity.

Appropriate clinical, diagnostic, and laboratory measures to attempt to delineate the cause of the adverse reaction in question must be performed and the results reported. All tests that reveal an abnormality considered to be related to adoptive transfer will be repeated at appropriate intervals until the course is determined or a return to normal values occurs.

8. Statistical Considerations

The considerations for the Phase I study of CD8+ cytotoxic T cells genetically modified to express a CD19-specific chimeric Inimunoreceptor and HyTK for re-directed pre-B ALL targeting administered to research participants who suffer a relapse of their CD19+ ALL following HLA-matched allogeneic BMT are as follows. (a) Demographic and background characteristics obtained at enrollment are listed and summarized. (b) The type and grade of toxicities noted during therapy are summarized for each dose level. (c) All adverse events noted by the investigator are tabulated according to the affected body system. (d) Descriptive statistics are used to summarize the changes from baseline in clinical laboratory parameters. (e) For those patients with measurable tumor at the time T cell therapy commences, responses are be stratified per ALL response criteria (Table 5). (f) Kaplan-Meier product limit methodology are used to estimate the survival. (g) 95% confidence intervals are calculated for all described statistics.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

List of References

1. Horowitz, M. M. Uses and Growth of Hematopoietic Cell Transplantation. In: E. D. Thomas, et al. (eds.), *Hematopoietic Cell Transplantation*, pp. 12-18, Malden, Mass.: Blackwell Science, Inc. 1999.
2. Buckner, C. D. et al. *Prog.Hematol.,* 8:299-324: 299-324, 1973.
3. Santos, G. W. *Cancer,* 54: 2732-2740, 1984.
4. Graw, R. G. J. et al. *Lancet,* 2: 1053-1055, 1970.
5. Peterson, P. K. et al. *Infect. Control.,* 4: 81-89, 1983.
6. Smith, E. P. and Nademanee, A. *Clin.Transpl.,* 291-310, 1995.
7. Wingard, J. R. et al. *J.Clin. Oncol.,* 8: 820-830, 1990.
8. Forman, S. J. *Curr.Opin.Oncol.,* 10: 10-16, 1998.
9. Philip, T. and Biron, P. *Eur.J.Cancer,* 27:320-322, 1991.
10. Philip, T. et al. *N.Engl.J.Med.,* 316:1493-1498, 1987.
11. Sharp, J. G. et al. *J.Clin.Oncol.,* 14: 214-219, 1996.
12. Snyder, D. S. et al. *Leukemia,* 13(12):2053-8, 1999.
13. Radich, J. et al. *Blood,* 89(7): 2602-9, 1997.
14. Mitterbauer, G. et al. *Br J Haematol.,* 106(3): 634-43, 1999.
15. Sullivan, K. M. et al. *Prog.Clin.Biol.Res.,* 244:391-9: 391-399, 1987.
16. Horowitz, M. M. et al. *Blood,* 75: 555-562, 1990.
17. Gale, R. P. et al. *Ann.Intern.Med.,* 120: 646-652, 1994.
18. Korngold, R. and Sprent, J. *Immunol.Rev.,* 71:5-29: 5-29, 1983.
19. Berger, M. et al. *Transplantation,* 57: 1095-1102, 1994.
20. Truitt, R. L. and Atasoylu, A. A. *Bone Marrow Transplant.,* 8: 51-58, 1991.
21. Pion, S. et al. *J.Clin.Invest.,* 95: 1561-1568, 1995.
22. Bar, B. M. et al. *J.Clin.Oncol.,* 11: 513-519, 1993.
23. Kolb, H. J. et al. *Blood,* 86: 2041-2050, 1995.
24. Mackinnon, S. et al. *Blood,* 86: 1261-1268, 1995.
25. Flowers, M. E. D. et al. *Blood,* 22421995.(Abstract)
26. Tiberghien, P. et al. *Blood,* 84:1333-1341, 1994.
27. Bonini, C. et al. *Science,* 276: 1719-1724, 1997.
28. Warren, E. H. et al. *Blood,* 91: 2197-2207, 1998.
29. Warren, E. H. et al. *Curr.Opin.Hematol.,* 5: 429-433, 1998.
30. Bonnet, D. et al. *Proc Natl Acad Sci,* 96(15):8639-44, 1999.
31. Vervoordeldonk, S. F. et al. *Cancer,* 73:1006-1011, 1994.
32. Bubien, J. K. et al., *J.Cell Biol.,* 121: 1121-1132, 1993.
33. Tedder, T. F. et al., *Proc.Natl.Acad.Sci.USA,* 85: 208-212, 1988.
34. Press, O. W. et al., *Blood,* 83: 1390-1397, 1994.
35. Shan, D. et al., *Blood,* 91: 1644-1652, 1998.
36. Ghetie, M. A. et al., *Proc.Natl.Acad.Sci.USA,* 94: 7509-7514, 1997.
37. Maloney, D. G. et al., *Blood,* 90: 2188-2195, 1997.
38. McLaughlin, P. et al., *Journal of Clinical Oncology,* 16: 2825-2833, 1998.
39. Coiffier, B. et al., *Blood,* 92: 1927-1932, 1998.
40. Leget, G. A. and Czuczrman, M. S., *Curr.Opin.Oncol.,* 10: 548-551, 1998.
41. Tobinai, K. et al., *Ann. Oncol.,* 9: 527-534, 1998.
42. Liu, S. Y. et al., *J.Clin.Oncol.,* 16: 3270-3278, 1998.
43. Stamenkovic, I. and Seed, B., *J.Exp.Med.,* 168: 1205-1210, 1988.
44. Sato, S. et al. *J.Immunol.,* 159: 3278-3287, 1997.
45. Pulczynski, S. *Leuk.Lymphoma,* 15: 243-252, 1994.
46. Roy, D. C. et al., *J.Clin.Immunol.,* 15: 51-57, 1995.
47. Waddick, K. G. et al., *Blood,* 86: 4228-4233, 1995.
48. Myers, D. E. et al., *Proc.Natl.Acad.Sci.U.S.A.,* 92:9575-9579,1995. [published erratum appears in *Proc Natl Acad Sci USA* Feb. 6, 1996;93(3):1357].
49. Ghetie, M. A. et al., *Blood,* 83: 1329-1336, 1994.
50. Uckun, F. et al. *Blood,* 71(1): 13-29, 1988.
51. Uckun, F. et al., *J Exp Med.* 163: 347-369, 1986.
52. Myers, D. E. et al., *J.Immunol.Methods,* 136: 221-237, 1991.
53. Nguyen, D. T. et al., *Eur.J.Haematol.,* 62: 76-82, 1999.
54. Yee, C. et al., *Curr.Opin.Immunol.,* 9: 702-708, 1997.
55. Linehan, W. M. etal., *Semin.Urol.,* 11: 41-43, 1993.
56. Greenberg, P. D. *Adv.Immunol.,* 49:281-355, 1991.
57. Boon, T. et al., *Annu. Rev. Immunol.,* 12:337-65: 337-365, 1994.
58. Rosenberg, S. A. *Immunity,* 10: 281-287, 1999.
59. Bohlen, H. et al., *Blood,* 82: 1803-1812, 1993.
60. Haagen, I. A. et al., *Blood,* 84: 556-563, 1994.
61. Csoka, M. et al., *Leukemia,* 10: 1765-1772, 1996.
62. De Gast, G. C. et al., *J.Hematother.,* 4: 433-437, 1995.
63. De Gast, G. C. et al., *Cancer Immunol. Immunother.,* 40: 390-396, 1995. [published erratum appears in Proc Natl Acad Sci USA 1996 Feb. 6;93(3):1357].
64. Li, C. R. et al., *Blood.* 83(7): 1971-9, 1994.
65. Walter, E. A. et al., *N Engl J Med.* 333(16): 1038-44, 1995.
66. Heslop, H. E. et al., *Immunol.Rev.* 157:217, 1997
67. Greenberg, P. D. et al., *Cancer J.Sci.Am.* 4 Suppl 1:S100-5:S100, 1998
68. Wilson, C. A. et al., *Hum. Gene Ther.* 8:869, 1997
69. Smith, C. A. et al., *J.Hematother.* 4:73, 1995
70. Riddell, S. R. et al., *Nat.Med.* 2:216, 1996
71. Woffendin, C. et al., *Proc.Natl.Acad.Sci.U.S.A.* 93:2889, 1996
72. Eshhar, Z. et al., *Proc.Natl.Acad.Sci.U.S.A.* 90:720, 1993
73. Stancovski, I. et al., *J.Immunol.* 151:6577, 1993
74. Darcy, P. K. et al., *Eur.J.Immunol.* 28:1663, 1998
75. Moritz, D. et al., *Proc.Natl.Acad.Sci.U.S.A.* 91:4318, 1994
76. Hekele, A. et al., *Int.J.Cancer* 68:232, 1996
77. Bolhuis, R. L. et al., *Adv.Exp.Med.Biol.* 451:547-55:547, 1998
78. Altenschmidt, U. et al., *J.Immunol.* 159:5509, 1997
79. Weijtens, M. E. et al., *J.Immunol.* 157:836, 1996

80. Jensen, M. et al., *Biol.Blood Marrow Transplant.* 4:75, 1998
81. Jensen, M. C. et al., *Molecular Therapy* 1(1):49-55, 2000
82. Chu, G. et al. *Nucleic.Acids.Res.* 15:1311, 1987
83. Nicholson, I. C. et al., *Mol. Immunol.* 34(16-17):1157-65, 1997.
84. Gross et al., *FASEB J* 6:3370, 1992.
85. Hwu et al., *Cancer Res.* 55:3369, 1995.
86. Riddell et al., *Science* 257:238, 1992.
87. Heslop et al., *Nat. Med.* 2:551, 1996.
88. Rosenberg et al., *J. Natl. Cancer Inst* 85:622, 1993.
89. Rosenberg et al., *J. Natl. Cancer Inst* 85:1091, 1993.
90. Rosenberg et. al., *N. Engl. J. Med.* 319:1676, 1988.
91. Van Pel et al., *Immunol. Rev.* 145:229, 1995.
92. Porter et al., *Cancer Treat Res.* 77:57, 1997.
93. van Lochem et al., *Bone Marrow Transplant.* 10:181, 1992.
94. Cardoso et al., *Blood* 90:549, 1997.
95. Dolstra et al., *J. Immunol.* 158:560, 1997.
96. Dohi et al., *J. Immunol.* 135:47, 1985.
97. Chakrabarti et al., *Cell Immunol.* 144:455, 1992.
98. Irving et al., *Cell* 64:891, 1991.
99. Bird et al., *Science* 242:423, 1988.
100. Bird et al., *Science* 244:409, 1989.
101. Gross et al., *Biochem. Soc. Trans.* 23:1079, 1995.
102. Glimcher et al., *J Exp Med.* 155:445-59, 1982.
103. Roberts, et al. *J. Immunol.* 161(1):375-84, 1998
104. Maniatis. T., et al. Molecular Cloning: *A Laboratory Manual* (Cold Spring Harbor Laboratory, Cold Spring Harbor, N.Y.) 1982.
105. Sambrook, J., et al. Molecular Cloning: *A Laboratory Manual*, 2nd Ed. (Cold Spring Harbor Laboratory, Cold Spring Harbor, N.Y.) 1989.
106. Ausubel, F. M., et al. *Current Protocols in Molecular Biology*, (J. Wiley and Sons, NY) 1992.
107. Glover, D. DNA Cloning, I and II (Oxford Press). 1985.
108. Anand, R. Techniques for the Analysis of Complex Genomes, (Academic Press) 1992.
109. Guthrie, G. and Fink, G. R. Guide to Yeast Genetics and Molecular Biology (Academic Press). 1991.
110. Harlow and Lane. Antibodies: *A Laboratory Manual* (Cold Spring Harbor Laboratory, Cold Spring Harbor, N.Y.) 1989.
111. Jakoby, W. B. and Pastan, I. H. (eds.) Cell Culture. *Methods in Enzymology*, Vol. 58 (Academic Press, Inc., Harcourt Brace Jovanovich (NY) 1979.
112. *Nucleic Acid Hybridization* (B. D. Hames & S. J. Higgins eds.) 1984.
113. *Transcription And Translation* (B. D. Hames & S. J. Higgins eds.) 1984.
114. *Culture Of Animal Cells* (R. I. Freshney, Alan R. Liss, Inc.) 1987.
115. *Immobilized Cells And Enzymes* (IRL Press) 1986.
116. B. Perbal, *A Practical Guide To Molecular Cloning* 1984.
117. *Methods In Enzymology* (Academic Press, Inc., N.Y.)
118. *Gene Transfer Vectors For Mammalian Cells* (J. H. Miller and M. P. Calos eds., Cold Spring Harbor Laboratory) 1987.
119. *Methods In Enzymology*, Vols. 154 and 155 (Wu et al. eds.), *Immunochemical Methods In Cell And Molecular Biology* (Mayer and Walker, eds., Academic Press, London) 1987.
120. *Handbook Of Experimental Immunology*, Volumes I-IV (D. M. Weir and C. C. Blackwell, eds.) 1986.
121. Hogan et al., Manipulating the Mouse Embryo, (Cold Spring Harbor Laboratory Press, Cold Spring Harbor, N.Y.) 1986.

---

What is claimed is:

1. A CD19-specific chimeric T cell receptor which comprises scFvFc:ζ, wherein scFvFc represents the extracellular domain, scFv represents the $V_H$ and $V_L$ chains of a single chain monoclonal antibody to CD19, Fc represents at least part of a constant region of an $IgG_1$, and ζ represents the effector function intracellular signaling domain of the zeta chain of human CD3, wherein the extracellular domain and the intracellular domain are linked by the transmembrane domain of human CD4 and wherein the chimeric receptor comprises amino acids 23-634 of SEG ID NO:2.

2. Genetically engineered CD19-specific T cells which express and bear on the cell surface membrane the CD19-specific chimeric receptor of claim 1.

3. The genetically engineered CD19-specific T cells of claim 2 which are $CD4^+$ and which produce IL-2 when co-cultured in vitro with $CD19^+$ malignant B cells.

4. The genetically engineered CD19-specific T cells of claim 2 which are $CD8^+$ or $CD4^+$ and which lyse $CD19^+$ target malignant B-cells when co-cultured in vitro with the target cells.

5. The genetically engineered CD19-specific T cells of claim 2 which comprises a mixed population of $CD4^+$ and $CD8^+$ cells.

* * * * *

UNITED STATES PATENT AND TRADEMARK OFFICE
CERTIFICATE OF CORRECTION

PATENT NO. : 7,446,179 B2
APPLICATION NO. : 10/416011
DATED : November 4, 2008
INVENTOR(S) : Jensen et al.

It is certified that error appears in the above-identified patent and that said Letters Patent is hereby corrected as shown below:

On the Title Page item (75),

First named inventor: "Micahel" should be "Michael"

On the Title Page, item (57),

Line 3, insert a period between "receptor" and "The"

Line 5, "CD9" should be "CD19"

Line 15, "SEQ I DNO:2." should be "SEQ ID NO:2."

Col. 5, line 20, "gancyclovir" should be "ganciclovir"

Col. 6, line 12, "scFvFc:zζ" should be "scFvFc:ζ"

Col. 12, line 22, "scfv" should be "scFv"

Col. 12, line 26, "moleculer" should be "molecular"

Col. 13, line 3, delete second instance of "cell lines"

Col. 13, line 30, "gancyclovir[+]" should be "gangiclovir"

Col. 13, line 35, "autoimmunie" should be "autoimmune"

Col. 13, line 59, insert "be" between "can" and "about"

Col. 14, line 40, delete "in" between "forth" and "together"

Col. 14, line 66, "confinmed" should be "confirmed"

Col. 15, line 21, "leukemmia" should be "leukemia"

Col. 15, line 24, "lonomycin" should be "Ionomycin"

UNITED STATES PATENT AND TRADEMARK OFFICE
CERTIFICATE OF CORRECTION

PATENT NO. : 7,446,179 B2
APPLICATION NO. : 10/416011
DATED : November 4, 2008
INVENTOR(S) : Jensen et al.

It is certified that error appears in the above-identified patent and that said Letters Patent is hereby corrected as shown below:

Col. 15, line 30, "responsder" should be "responder"

Col. 15, line 54, "Antige-Specific" should be "Antigen-Specific"

Col. 18, line 18, "colummns" should be "columns"

Col. 19, line 6, "32P-labeled" should be "$^{32}$P-labeled"

Col. 19, line 41, "Acitivity" should be "Activity"

Col. 21, Table 1, Test for Sterility – delete first instance of "days" in the Release Criteria field Col. 21, Table 1, Test for Sterility – "cyropreservation" should be "cryopreservation" in the Release Criteria field Col. 21, line 42, "(70)" should be "(70)"

Col. 24, line 33, Table 2: "U/m2/dose" should be "U/m$^2$/dose"

Col. 24, line 46, delete "for" between "bag" and "suitable"

Col. 25, line 26, "Proleulin" should be "Proleukin"

Col. 26, line 22, delete "http:"

Col. 28, line 29, "Pre-t" should be "Pre-T"

Col. 30, line 3, insert a period after "ing"

Col. 31, line 4, "Inimunoreceptor" should be "immunoreceptor"

Col. 31, line 33, Ref. 3, delete first instance of "299-324:"

Col. 31, line 49, Ref. 15, delete first instance of "391-9:"

UNITED STATES PATENT AND TRADEMARK OFFICE
CERTIFICATE OF CORRECTION

PATENT NO. : 7,446,179 B2
APPLICATION NO. : 10/416011
DATED : November 4, 2008
INVENTOR(S) : Jensen et al.

It is certified that error appears in the above-identified patent and that said Letters Patent is hereby corrected as shown below:

Col. 31, line 53, Ref. 18, delete first instance of "5-29:"

Col. 31, line 62, Ref. 25, "22421995" should be "2242, 1995"

Col. 32, line 15, Ref. 40, "Czuczrman" should be "Czuczman"

Col. 32, line 35, Ref. 55, "etal." should be "et al."

Col. 32, line 37, Ref. 57, delete first instance of "337-65:"

Signed and Sealed this

Twenty-fourth Day of February, 2009

JOHN DOLL
*Acting Director of the United States Patent and Trademark Office*

SEQUENCE LISTING

```
<160> NUMBER OF SEQ ID NOS: 8

<210> SEQ ID NO 1
<211> LENGTH: 1931
<212> TYPE: DNA
<213> ORGANISM: Artificial Sequence
<220> FEATURE:
<223> OTHER INFORMATION: CD19R: zeta chimeric receptor
<220> FEATURE:
<221> NAME/KEY: CDS
<222> LOCATION: (19)..(1920)
<223> OTHER INFORMATION:

<400> SEQUENCE: 1
atctctagag ccgccacc atg ctt ctc ctg gtg aca agc ctt ctg ctc tgt        51
                    Met Leu Leu Leu Val Thr Ser Leu Leu Leu Cys
                    1               5                   10 gag tta cca cac cca gca ttc ctc ctg atc cca gac atc cag atg aca        99
Glu Leu Pro His Pro Ala Phe Leu Leu Ile Pro Asp Ile Gln Met Thr
            15                  20                  25 cag act aca tcc tcc ctg tct gcc tct ctg gga gac aga gtc acc atc       147
Gln Thr Thr Ser Ser Leu Ser Ala Ser Leu Gly Asp Arg Val Thr Ile
        30                  35                  40 agt tgc agg gca agt cag gac att agt aaa tat tta aat tgg tat cag       195
Ser Cys Arg Ala Ser Gln Asp Ile Ser Lys Tyr Leu Asn Trp Tyr Gln
    45                  50                  55
```

```
cag aaa cca gat gga act gtt aaa ctc ctg atc tac cat aca tca aga    243
Gln Lys Pro Asp Gly Thr Val Lys Leu Leu Ile Tyr His Thr Ser Arg
 60              65                  70                  75 tta cac tca gga gtc cca tca agg ttc agt ggc agt ggg tct gga aca    291
Leu His Ser Gly Val Pro Ser Arg Phe Ser Gly Ser Gly Ser Gly Thr
                 80                  85                  90 gat tat tct ctc acc att agc aac ctg gag caa gaa gat att gcc act    339
Asp Tyr Ser Leu Thr Ile Ser Asn Leu Glu Gln Glu Asp Ile Ala Thr
             95                 100                 105 tac ttt tgc caa cag ggt aat acg ctt ccg tac acg ttc gga ggg ggg    387
Tyr Phe Cys Gln Gln Gly Asn Thr Leu Pro Tyr Thr Phe Gly Gly Gly
         110                 115                 120 act aag ttg gaa ata aca ggc tcc acc tct gga tcc ggc aag ccc gga    435
Thr Lys Leu Glu Ile Thr Gly Ser Thr Ser Gly Ser Gly Lys Pro Gly
     125                 130                 135 tct ggc gag gga tcc acc aag ggc gag gtg aaa ctg cag gag tca gga    483
Ser Gly Glu Gly Ser Thr Lys Gly Glu Val Lys Leu Gln Glu Ser Gly
140                 145                 150                 155 cct ggc ctg gtg gcg ccc tca cag agc ctg tcc gtc aca tgc act gtc    531
Pro Gly Leu Val Ala Pro Ser Gln Ser Leu Ser Val Thr Cys Thr Val
                160                 165                 170 tca ggg gtc tca tta ccc gac tat ggt gta agc tgg att cgc cag cct    579
Ser Gly Val Ser Leu Pro Asp Tyr Gly Val Ser Trp Ile Arg Gln Pro
            175                 180                 185 cca cga aag ggt ctg gag tgg ctg gga gta ata tgg ggt agt gaa acc    627
Pro Arg Lys Gly Leu Glu Trp Leu Gly Val Ile Trp Gly Ser Glu Thr
        190                 195                 200 aca tac tat aat tca gct ctc aaa tcc aga ctg acc atc atc aag gac    675
Thr Tyr Tyr Asn Ser Ala Leu Lys Ser Arg Leu Thr Ile Ile Lys Asp
    205                 210                 215 aac tcc aag agc caa gtt ttc tta aaa atg aac agt ctg caa act gat    723
Asn Ser Lys Ser Gln Val Phe Leu Lys Met Asn Ser Leu Gln Thr Asp
220                 225                 230                 235 gac aca gcc att tac tac tgt gcc aaa cat tat tac tac ggt ggt agc    771
Asp Thr Ala Ile Tyr Tyr Cys Ala Lys His Tyr Tyr Tyr Gly Gly Ser
                240                 245                 250 tat gct atg gac tac tgg ggt caa gga acc tca gtc acc gtc tcc tca    819
Tyr Ala Met Asp Tyr Trp Gly Gln Gly Thr Ser Val Thr Val Ser Ser
            255                 260                 265 gta gaa ccc aaa tct tct gac aaa act cac acg tgc cca ccg tgc cca    867
Val Glu Pro Lys Ser Ser Asp Lys Thr His Thr Cys Pro Pro Cys Pro
        270                 275                 280 gca cct gaa ctc ctg ggg gga ccg tca gtc ttc ctc ttc ccc cca aaa    915
Ala Pro Glu Leu Leu Gly Gly Pro Ser Val Phe Leu Phe Pro Pro Lys
    285                 290                 295 ccc aag gac acc ctc atg atc tcc cgg acc cct gag gtc aca tgc gtg    963
Pro Lys Asp Thr Leu Met Ile Ser Arg Thr Pro Glu Val Thr Cys Val
300                 305                 310                 315 gtg gtg gac gtg agc cac gaa gac cct gag gtc aag ttc aac tgg tac   1011
Val Val Asp Val Ser His Glu Asp Pro Glu Val Lys Phe Asn Trp Tyr
                320                 325                 330 gtg gac ggc gtg gag gtg cat aat gcc aag aca aag ccg cgg gag gag   1059
Val Asp Gly Val Glu Val His Asn Ala Lys Thr Lys Pro Arg Glu Glu
            335                 340                 345 cag tac aac agc acg tac cgt gtg gtc agc gtc ctc acc gtc ctg cac   1107
Gln Tyr Asn Ser Thr Tyr Arg Val Val Ser Val Leu Thr Val Leu His
        350                 355                 360 cag gac tgg ctg aat ggc aag gag tac aag tgc aag gtc tcc aac aaa   1155
Gln Asp Trp Leu Asn Gly Lys Glu Tyr Lys Cys Lys Val Ser Asn Lys
    365                 370                 375
```

```
gcc ctc cca gcc ccc atc gag aaa acc atc tcc aaa gcc aaa ggg cag    1203
Ala Leu Pro Ala Pro Ile Glu Lys Thr Ile Ser Lys Ala Lys Gly Gln
380             385                 390                 395 ccc cga gaa cca cag gtg tac acc ctg cca cca tca cga gat gag ctg    1251
Pro Arg Glu Pro Gln Val Tyr Thr Leu Pro Pro Ser Arg Asp Glu Leu
                400                 405                 410 acc aag aac cag gtc agc ctg acc tgc ctg gtc aaa ggc ttc tat ccc    1299
Thr Lys Asn Gln Val Ser Leu Thr Cys Leu Val Lys Gly Phe Tyr Pro
            415                 420                 425 agc gac atc gcc gtg gag tgg gag agc aat ggg cag ccg gag aac aac    1347
Ser Asp Ile Ala Val Glu Trp Glu Ser Asn Gly Gln Pro Glu Asn Asn
        430                 435                 440 tac aag acc acg cct ccc gtg ctg gac tcc gac ggc tcc ttc ttc ctc    1395
Tyr Lys Thr Thr Pro Pro Val Leu Asp Ser Asp Gly Ser Phe Phe Leu
    445                 450                 455 tac agc aag ctc acc gtg gac aag agc agg tgg cag cag ggg aac gtc    1443
Tyr Ser Lys Leu Thr Val Asp Lys Ser Arg Trp Gln Gln Gly Asn Val
460                 465                 470                 475 ttc tca tgc tcc gtg atg cat gag gct ctg cac aac cac tac acg cag    1491
Phe Ser Cys Ser Val Met His Glu Ala Leu His Asn His Tyr Thr Gln
                480                 485                 490 aag agc ctc tcc ctg tct ccc ggg aaa atg gcc ctg att gtg ctg ggg    1539
Lys Ser Leu Ser Leu Ser Pro Gly Lys Met Ala Leu Ile Val Leu Gly
                495                 500                 505 ggc gtc gcc ggc ctc ctg ctt ttc att ggg cta ggc atc ttc ttc aga    1587
Gly Val Ala Gly Leu Leu Leu Phe Ile Gly Leu Gly Ile Phe Phe Arg
            510                 515                 520 gtg aag ttc agc agg agc gca gac gcc ccc gcg tac cag cag ggc cag    1635
Val Lys Phe Ser Arg Ser Ala Asp Ala Pro Ala Tyr Gln Gln Gly Gln
        525                 530                 535 aac cag ctc tat aac gag ctc aat cta gga cga aga gag gag tac gat    1683
Asn Gln Leu Tyr Asn Glu Leu Asn Leu Gly Arg Arg Glu Glu Tyr Asp
540                 545                 550                 555 gtt ttg gac aag aga cgt ggc cgg gac cct gag atg ggg gga aag ccg    1731
Val Leu Asp Lys Arg Arg Gly Arg Asp Pro Glu Met Gly Gly Lys Pro
                560                 565                 570 aga agg aag aac cct cag gaa ggc ctg tac aat gaa ctg cag aaa gat    1779
Arg Arg Lys Asn Pro Gln Glu Gly Leu Tyr Asn Glu Leu Gln Lys Asp
            575                 580                 585 aag atg gcg gag gcc tac agt gag att ggg atg aaa ggc gag cgc cgg    1827
Lys Met Ala Glu Ala Tyr Ser Glu Ile Gly Met Lys Gly Glu Arg Arg
        590                 595                 600 agg ggc aag ggg cac gat ggc ctt tac cag ggt ctc agt aca gcc acc    1875
Arg Gly Lys Gly His Asp Gly Leu Tyr Gln Gly Leu Ser Thr Ala Thr
    605                 610                 615 aag gac acc tac gac gcc ctt cac atg cag gcc ctg ccc cct cgc        1920
Lys Asp Thr Tyr Asp Ala Leu His Met Gln Ala Leu Pro Pro Arg
620                 625                 630 taagcggccg c                                                       1931
```

<210> SEQ ID NO 2
<211> LENGTH: 634
<212> TYPE: PRT
<213> ORGANISM: Artificial Sequence
<220> FEATURE:
<223> OTHER INFORMATION: CD19R: zeta chimeric receptor

<400> SEQUENCE: 2

```
Met Leu Leu Leu Val Thr Ser Leu Leu Leu Cys Glu Leu Pro His Pro
1               5                   10                  15
```

-continued

```
Ala Phe Leu Leu Ile Pro Asp Ile Gln Met Thr Gln Thr Thr Ser Ser
             20                  25                  30

Leu Ser Ala Ser Leu Gly Asp Arg Val Thr Ile Ser Cys Arg Ala Ser
         35                  40                  45

Gln Asp Ile Ser Lys Tyr Leu Asn Trp Tyr Gln Gln Lys Pro Asp Gly
     50                  55                  60

Thr Val Lys Leu Leu Ile Tyr His Thr Ser Arg Leu His Ser Gly Val
 65                  70                  75                  80

Pro Ser Arg Phe Ser Gly Ser Gly Ser Gly Thr Asp Tyr Ser Leu Thr
                 85                  90                  95

Ile Ser Asn Leu Glu Gln Glu Asp Ile Ala Thr Tyr Phe Cys Gln Gln
             100                 105                 110

Gly Asn Thr Leu Pro Tyr Thr Phe Gly Gly Gly Thr Lys Leu Glu Ile
         115                 120                 125

Thr Gly Ser Thr Ser Gly Ser Gly Lys Pro Gly Ser Gly Glu Gly Ser
     130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Val Glu Pro Lys Ser
            260                 265                 270

Ser Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430
```

```
Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys Met Ala Leu Ile Val Leu Gly Gly Val Ala Gly Leu
            500                 505                 510

Leu Leu Phe Ile Gly Leu Gly Ile Phe Phe Arg Val Lys Phe Ser Arg
            515                 520                 525

Ser Ala Asp Ala Pro Ala Tyr Gln Gln Gly Gln Asn Gln Leu Tyr Asn
            530                 535                 540

Glu Leu Asn Leu Gly Arg Arg Glu Glu Tyr Asp Val Leu Asp Lys Arg
545                 550                 555                 560

Arg Gly Arg Asp Pro Glu Met Gly Gly Lys Pro Arg Arg Lys Asn Pro
                565                 570                 575

Gln Glu Gly Leu Tyr Asn Glu Leu Gln Lys Asp Lys Met Ala Glu Ala
            580                 585                 590

Tyr Ser Glu Ile Gly Met Lys Gly Glu Arg Arg Arg Gly Lys Gly His
            595                 600                 605

Asp Gly Leu Tyr Gln Gly Leu Ser Thr Ala Thr Lys Asp Thr Tyr Asp
            610                 615                 620

Ala Leu His Met Gln Ala Leu Pro Pro Arg
625                 630

<210> SEQ ID NO 3
<211> LENGTH: 29
<212> TYPE: DNA
<213> ORGANISM: Artificial Sequence
<220> FEATURE:
<223> OTHER INFORMATION: 5' scFvFc PCR primer

<400> SEQUENCE: 3
tcttcctcta cacagcaagc tcaccgtgg                                      29

<210> SEQ ID NO 4
<211> LENGTH: 24
<212> TYPE: DNA
<213> ORGANISM: Artificial Sequence
<220> FEATURE:
<223> OTHER INFORMATION: 3' human zeta chain PCR primer

<400> SEQUENCE: 4
gagggttctt ccttctcggc tttc                                           24

<210> SEQ ID NO 5
<211> LENGTH: 25
<212> TYPE: DNA
<213> ORGANISM: Artificial Sequence
<220> FEATURE:
<223> OTHER INFORMATION: 5'FAM-3' TAMRA labeled hybridization probe

<400> SEQUENCE: 5
ttcactctga agaagatgcc tagcc                                          25

<210> SEQ ID NO 6
<211> LENGTH: 20
<212> TYPE: DNA
```

```
<213> ORGANISM: Artificial Sequence
<220> FEATURE:
<223> OTHER INFORMATION: human betaglobin 5'PCR primer

<400> SEQUENCE: 6
acacaactgt gttcactagc                                              20

<210> SEQ ID NO 7
<211> LENGTH: 20
<212> TYPE: DNA
<213> ORGANISM: Artificial Sequence
<220> FEATURE:
<223> OTHER INFORMATION: human betaglobin 3' PCR primer

<400> SEQUENCE: 7
gtctccttaa acctgtcttg                                              20

<210> SEQ ID NO 8
<211> LENGTH: 23
<212> TYPE: DNA
<213> ORGANISM: Artificial Sequence
<220> FEATURE:
<223> OTHER INFORMATION: 5' HEX-3' TAMRA labeled hybridization probe

<400> SEQUENCE: 8
acctgactcc tgaggagaag tct                                          23
```